(12) United States Patent
Green

(10) Patent No.: US 7,204,841 B2
(45) Date of Patent: *Apr. 17, 2007

(54) APPARATUS FOR SUTURING A BLOOD VESSEL

(76) Inventor: David T. Green, 40 Madison Hill, Fairfield, CT (US) 06430

( * ) Notice: Subject to any disclaimer, the term of this patent is extended or adjusted under 35 U.S.C. 154(b) by 627 days.

This patent is subject to a terminal disclaimer.

(21) Appl. No.: 10/460,331

(22) Filed: Jun. 12, 2003

(65) Prior Publication Data

US 2003/0233109 A1 Dec. 18, 2003

Related U.S. Application Data

(63) Continuation-in-part of application No. 10/252,808, filed on Sep. 23, 2002, now Pat. No. 7,041,119, which is a continuation-in-part of application No. 09/794,553, filed on Feb. 27, 2001, now Pat. No. 6,454,777.

(51) Int. Cl.
*A61B 17/06* (2006.01)
*A61B 17/062* (2006.01)

(52) U.S. Cl. .................. 606/139; 606/144; 606/148
(58) Field of Classification Search ................ 606/139, 606/144–148; 223/104
See application file for complete search history.

(56) References Cited

U.S. PATENT DOCUMENTS

| 5,152,769 | A | * | 10/1992 | Baber ..................... 606/145 |
| 5,437,681 | A | | 8/1995 | Meade et al. |
| 5,540,705 | A | | 7/1996 | Meade et al. |
| 5,653,718 | A | * | 8/1997 | Yoon ..................... 606/148 |
| 5,746,755 | A | | 5/1998 | Wood et al. |
| 5,766,183 | A | | 6/1998 | Sauer |
| 5,810,849 | A | | 9/1998 | Kontos |
| 5,820,631 | A | | 10/1998 | Nobles |

(Continued)

FOREIGN PATENT DOCUMENTS

DE  199 42 951 C1  9/1999

(Continued)

*Primary Examiner*—Glenn K. Dawson
*Assistant Examiner*—Amanda Adams
(74) *Attorney, Agent, or Firm*—Scott D. Wofsy; Edwards Angell Palmer & Dodge LLP

(57) ABSTRACT

A vascular suturing device is disclosed which includes an elongated tubular body defining opposed proximal and distal end portions and having a longitudinal axis extending therethrough, the body including an inner tubular member, an outer tubular member and a central tubular member disposed between the inner and outer tubular members. The inner tubular member and the central tubular member are mounted for movement relative to the outer tubular member about the longitudinal axis of the body for sequentially driving a pair of suture needles through the wall of a blood vessel to close an incision formed therein. A vascular dilator having a tapered distal tip portion is slidably supported within the inner tubular member and is dimensioned to extend beyond the distal end of the inner tubular member for positioning the suturing device at the incision in the wall of the blood vessel. The dilator is configured to move axially between an extended position and a retracted position. A biasing element and a retaining pin are associated with a proximal end of the dilator. The biasing element is adapted and configured for urging the dilator in the retracted position and the retaining pin is position so as to secure the dilator in the extended position.

24 Claims, 24 Drawing Sheets

U.S. PATENT DOCUMENTS

| | | |
|---|---|---|
| 5,830,125 A * | 11/1998 | Scribner et al. ............ 606/139 |
| 5,836,955 A | 11/1998 | Buelna et al. |
| 5,860,990 A | 1/1999 | Nobles et al. |
| 5,868,762 A | 2/1999 | Cragg et al. |
| 5,921,994 A | 7/1999 | Andrea et al. |
| 5,964,773 A | 10/1999 | Greenstein |
| 5,980,539 A | 11/1999 | Kontos |
| 5,984,932 A * | 11/1999 | Yoon .......................... 606/147 |
| 6,042,601 A | 3/2000 | Smith |
| 6,071,289 A | 6/2000 | Stefanchik et al. |
| 6,074,404 A | 6/2000 | Stalket et al. |
| 6,110,184 A | 8/2000 | Weadock |
| 6,117,144 A | 9/2000 | Nobles et al. |
| 6,368,334 B1 | 4/2002 | Sauer |
| 6,454,777 B1 * | 9/2002 | Green ........................ 606/144 |
| 7,041,119 B2 * | 5/2006 | Green ........................ 606/213 |
| 2003/0018345 A1 * | 1/2003 | Green ........................ 606/144 |

FOREIGN PATENT DOCUMENTS

| | | |
|---|---|---|
| EP | 0 552 430 A1 | 11/1992 |
| WO | WO 95/13021 | 5/1995 |
| WO | 97/27807 | 8/1997 |
| WO | 99/04697 | 2/1999 |

* cited by examiner

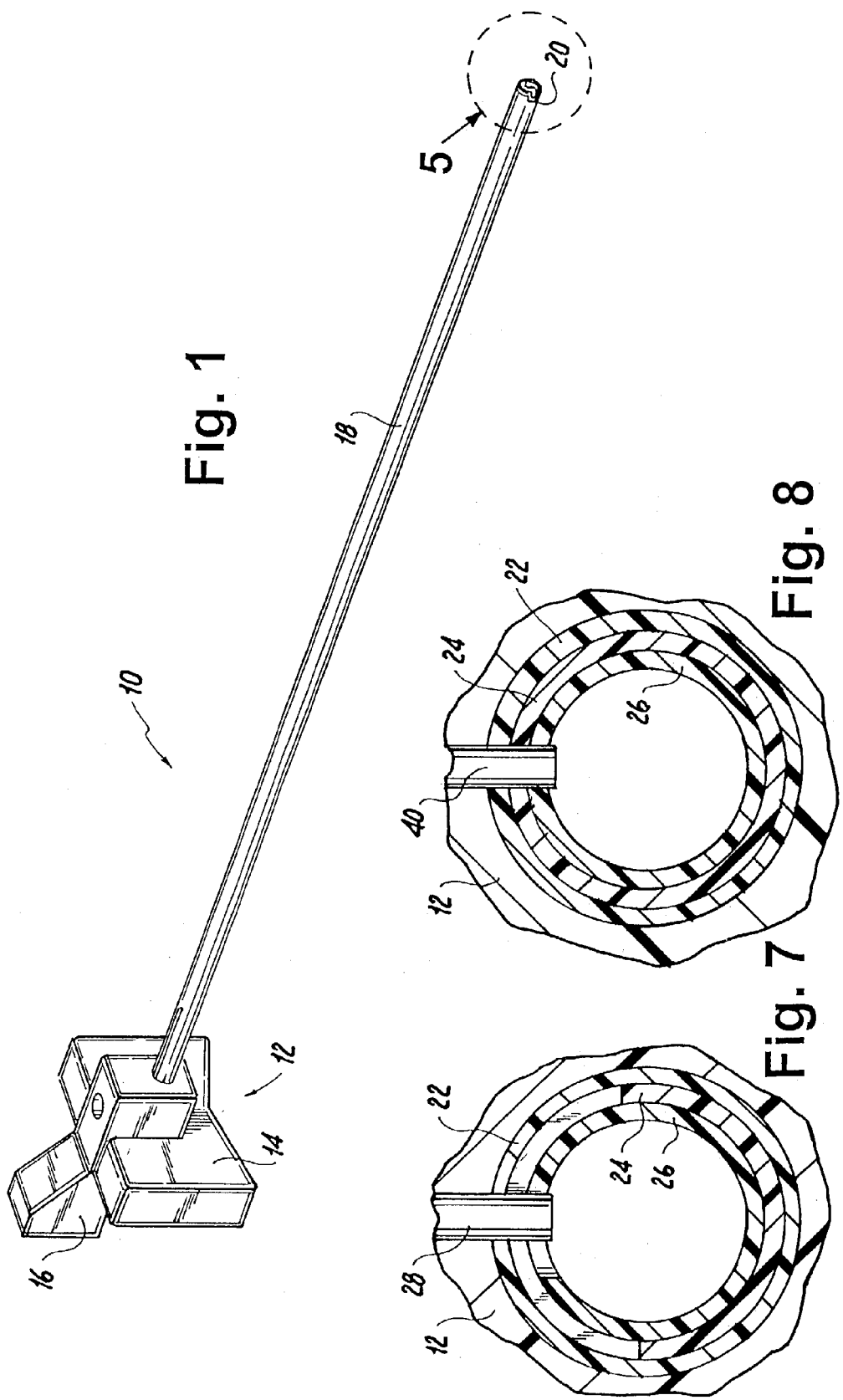

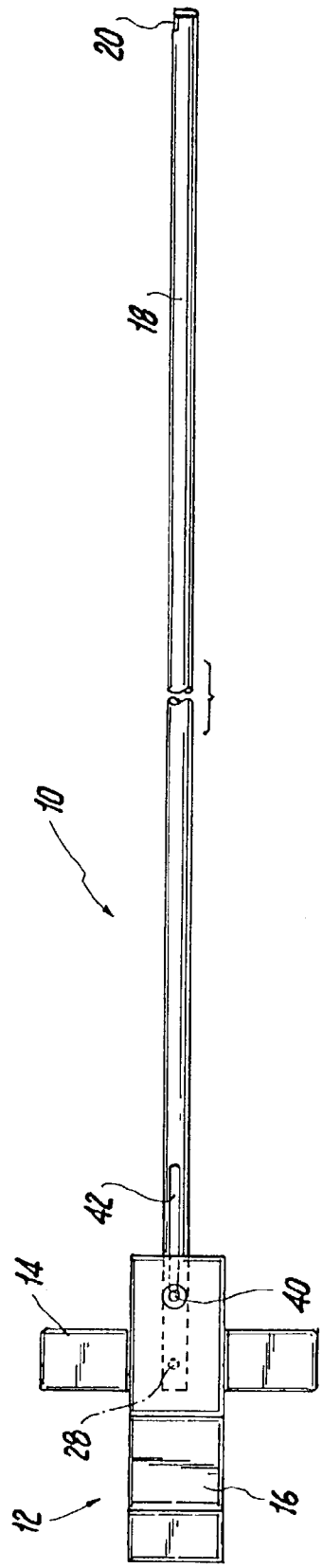
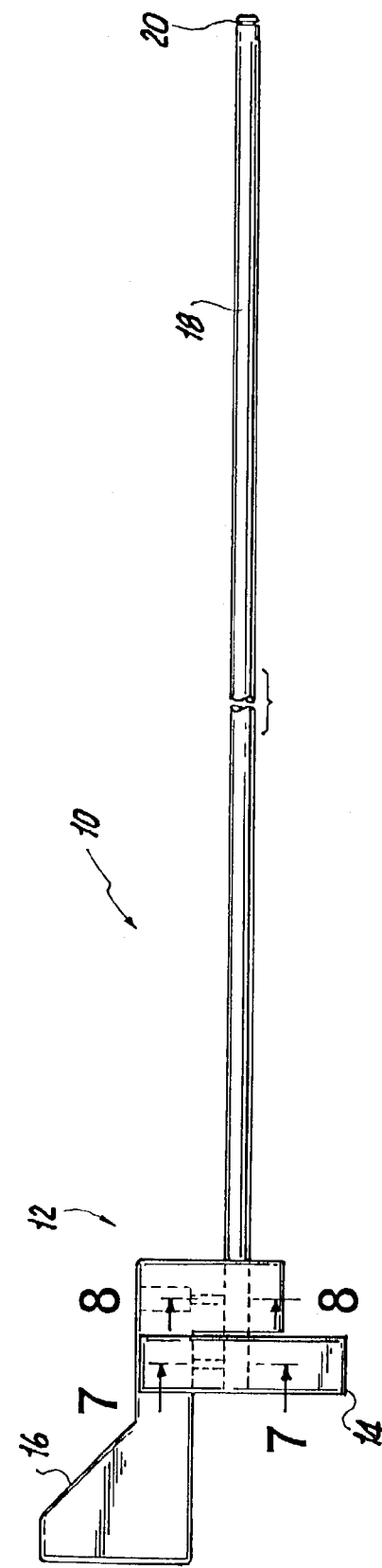

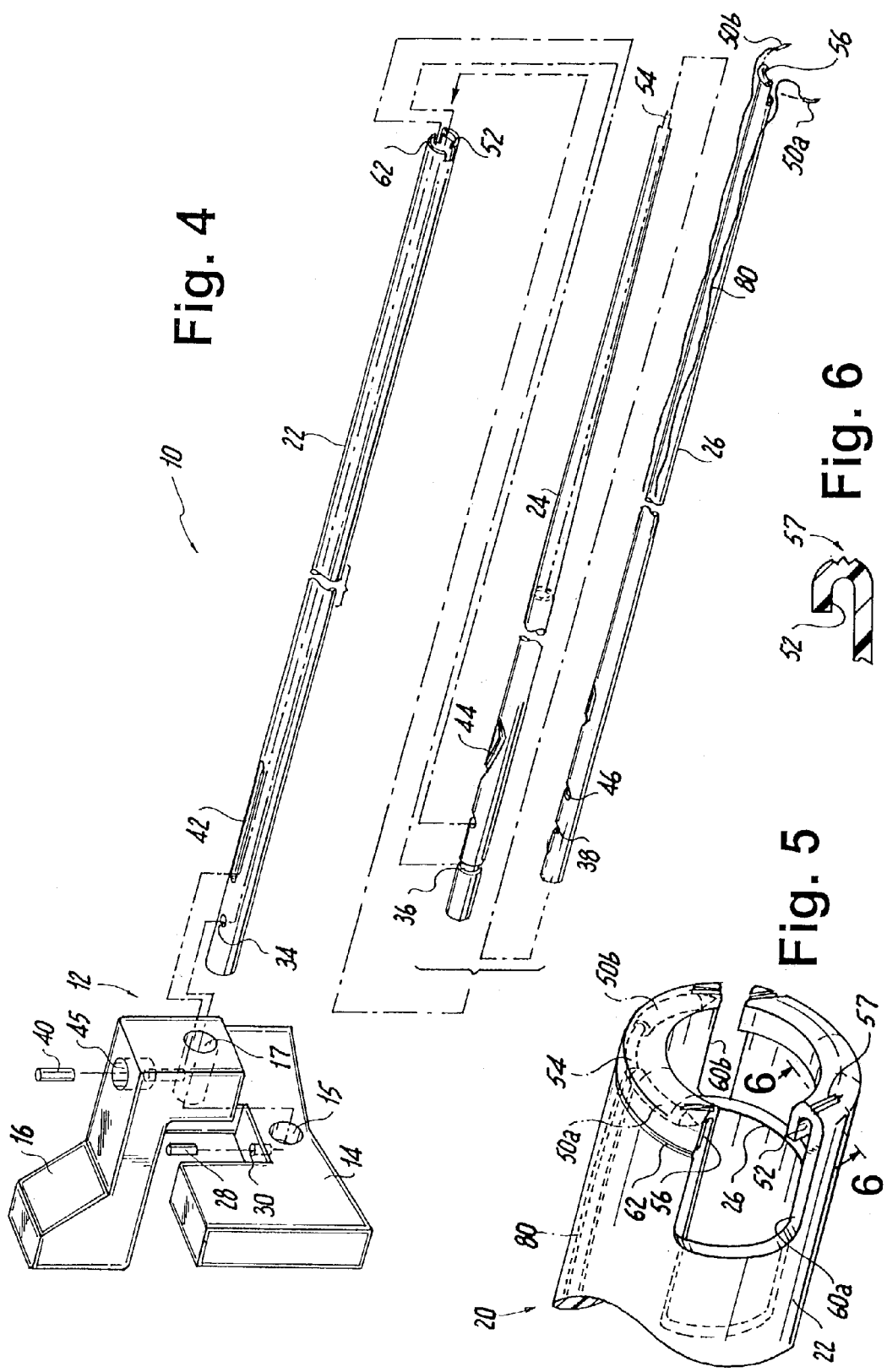

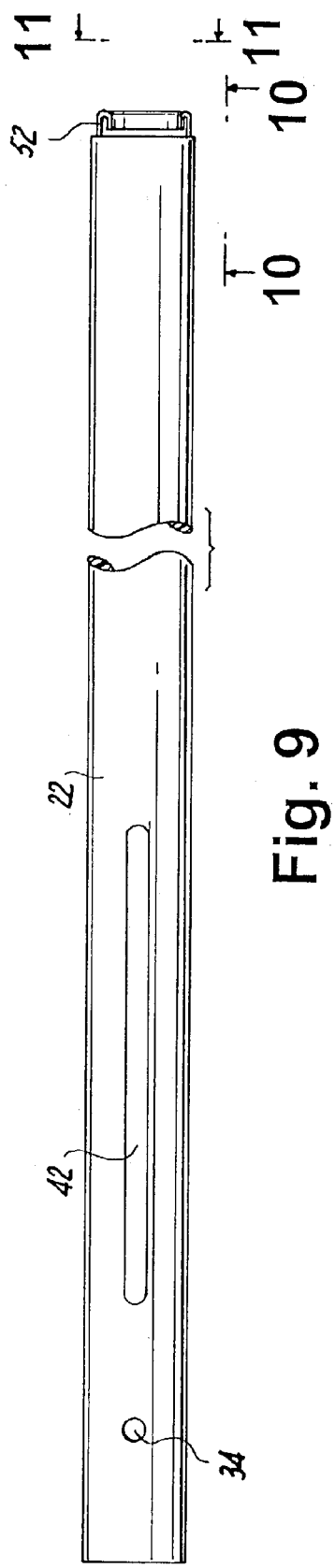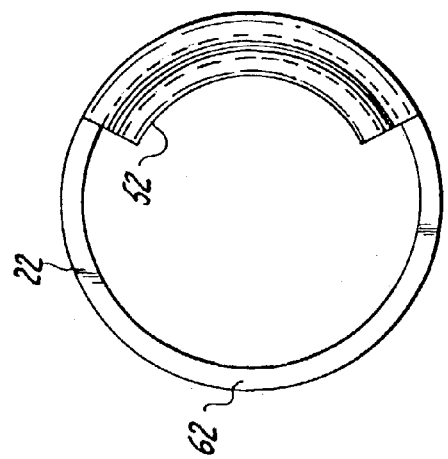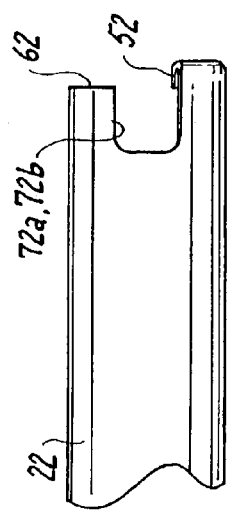
Fig. 9
Fig. 11
Fig. 10

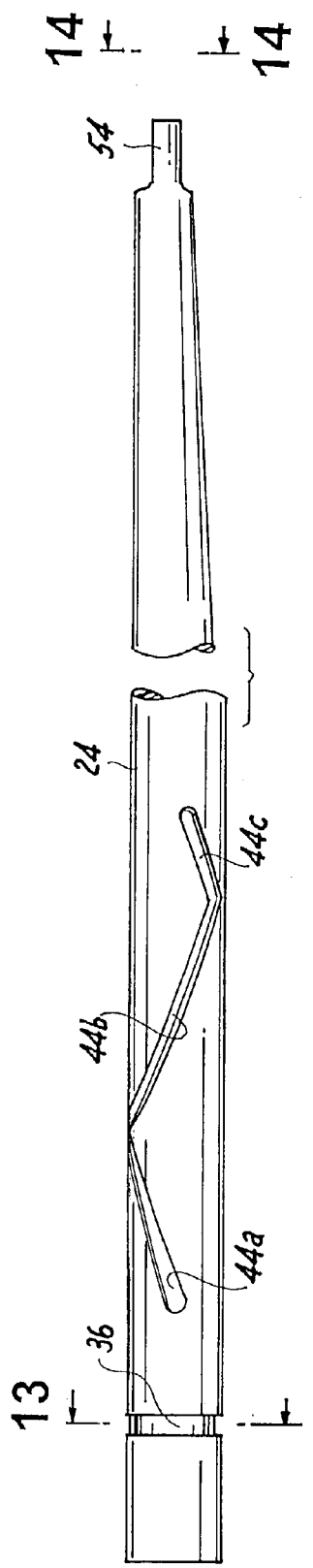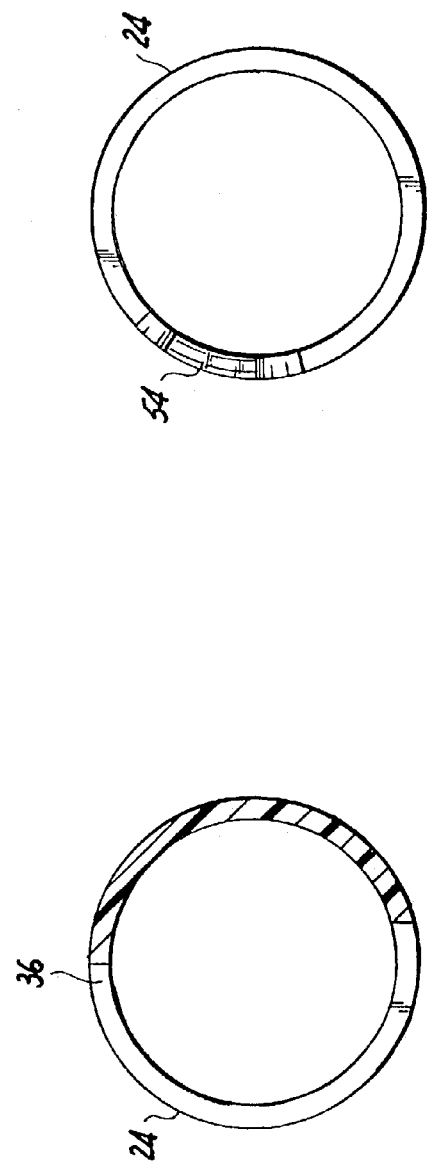
Fig. 12
Fig. 13
Fig. 14

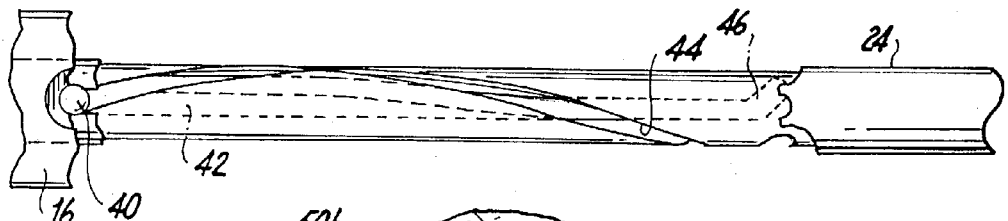
Fig. 22
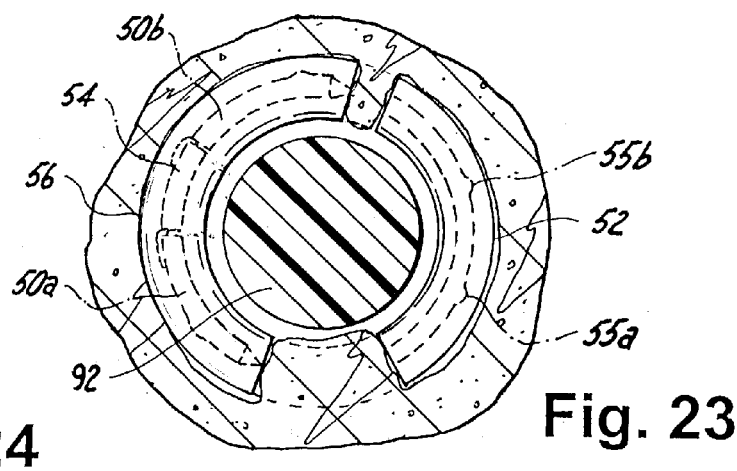
Fig. 24
Fig. 23
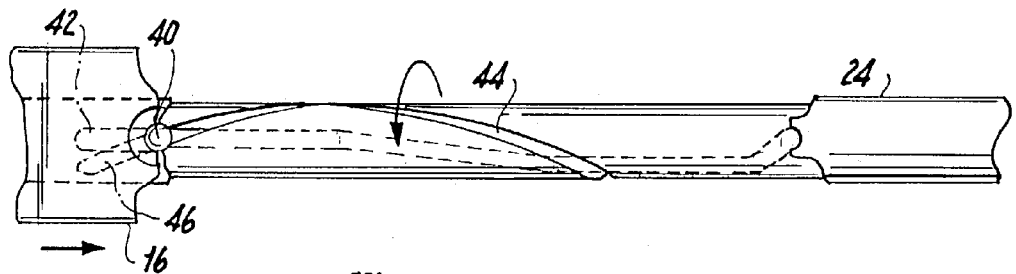
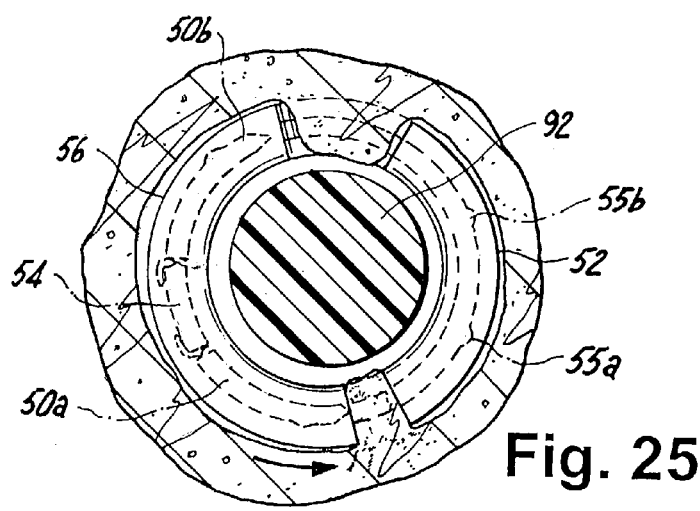
Fig. 25

Fig. 26
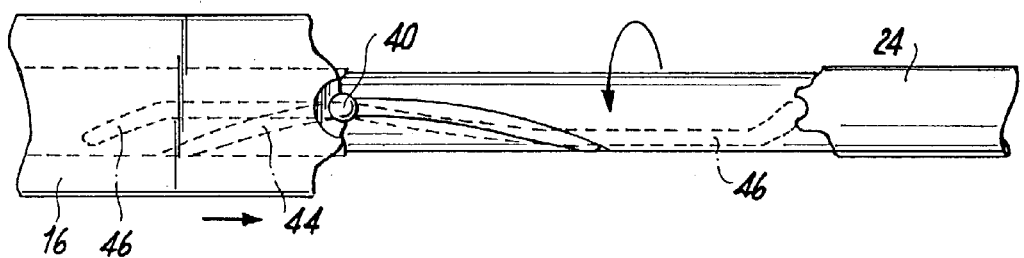
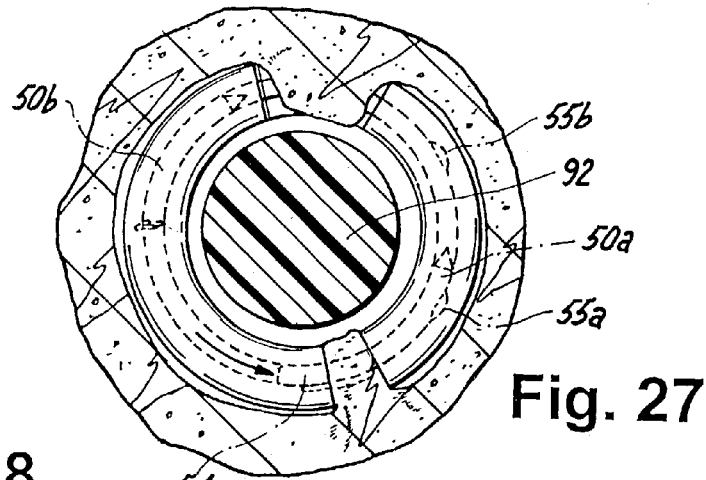
Fig. 27
Fig. 28
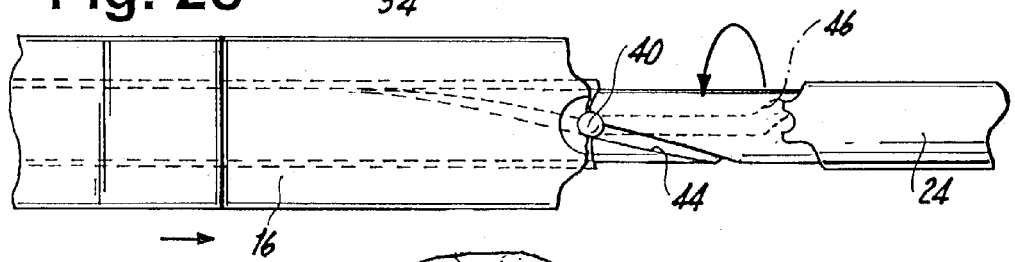
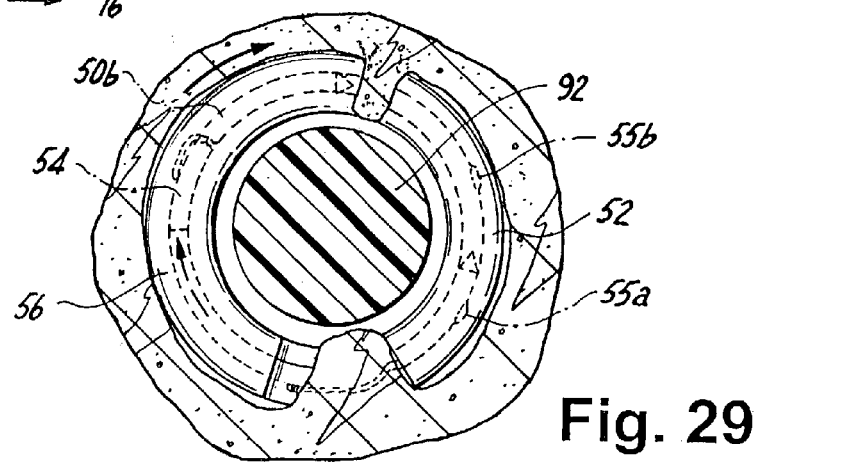
Fig. 29

Fig. 30
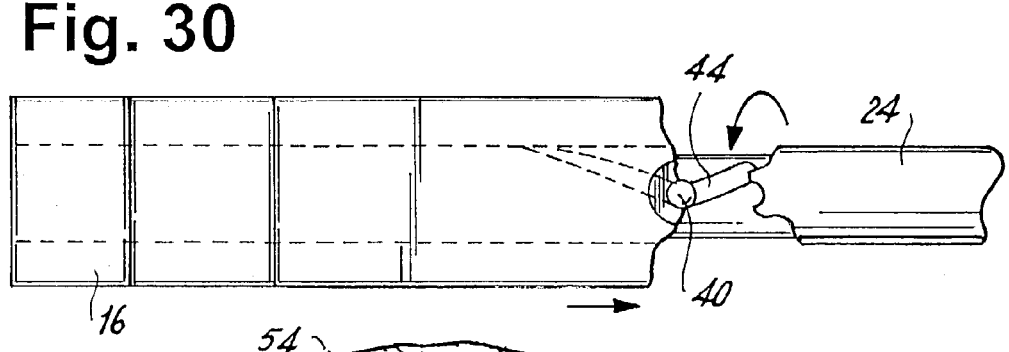
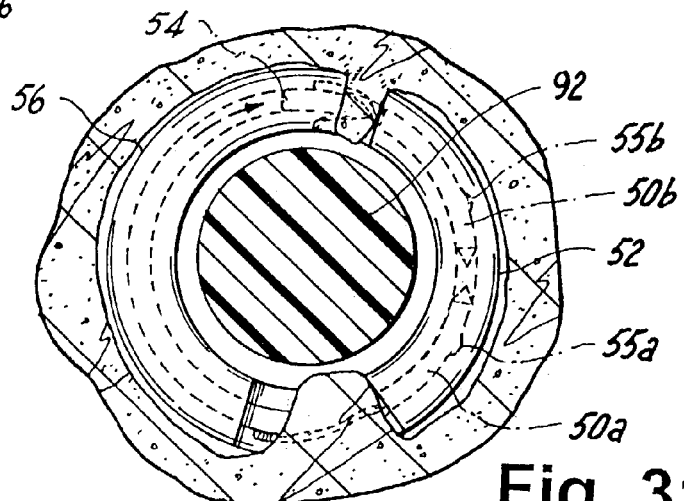
Fig. 31
Fig. 32
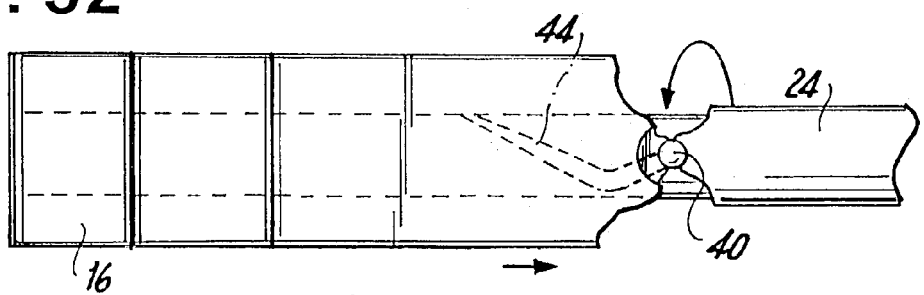
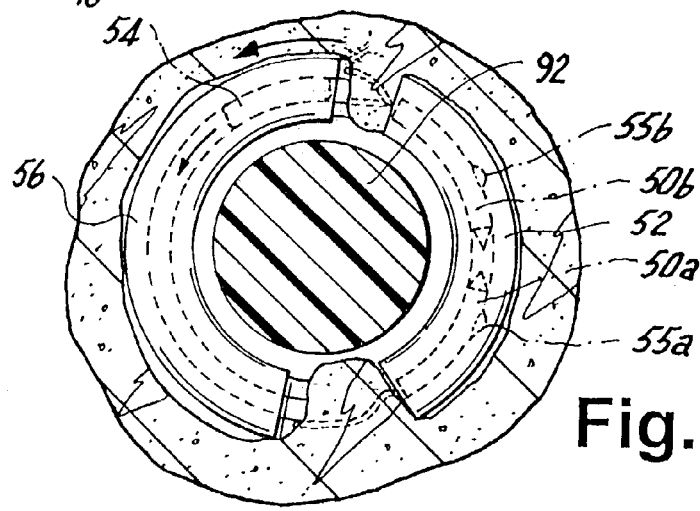
Fig. 33

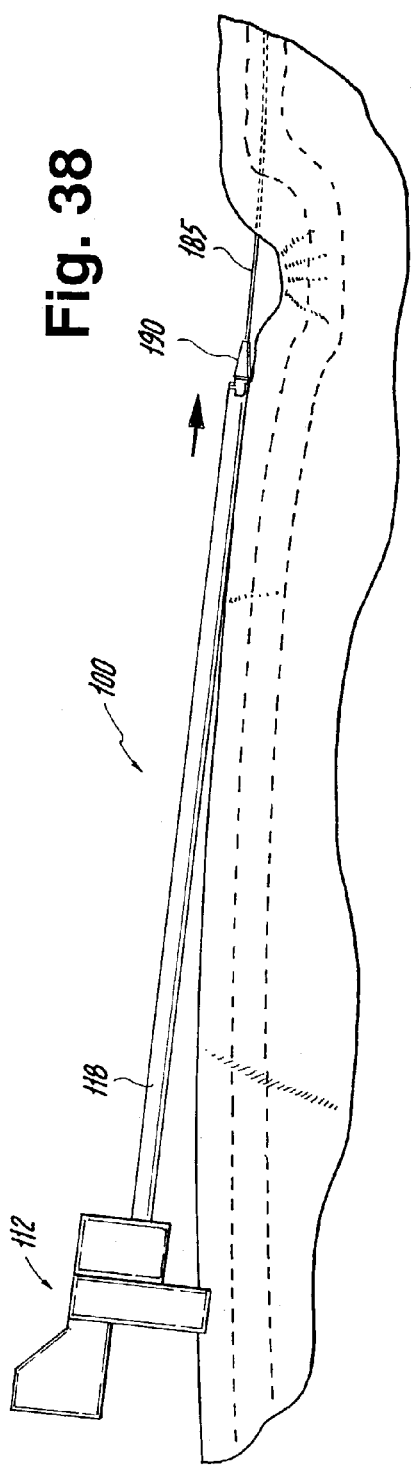
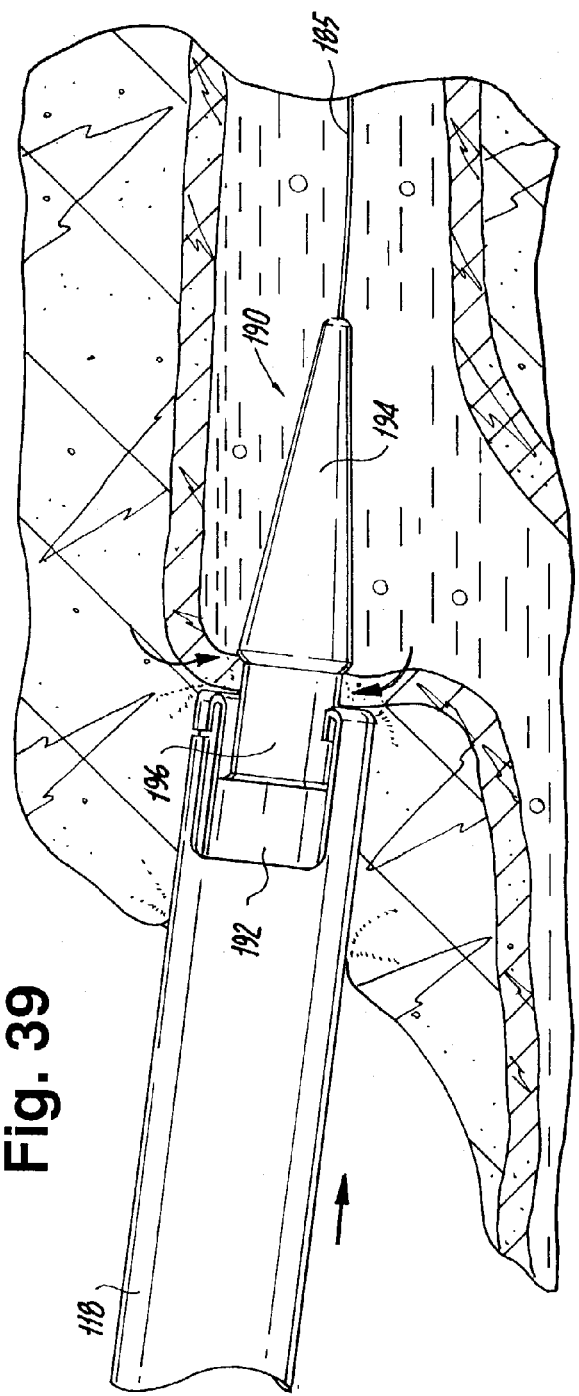
Fig. 38
Fig. 39

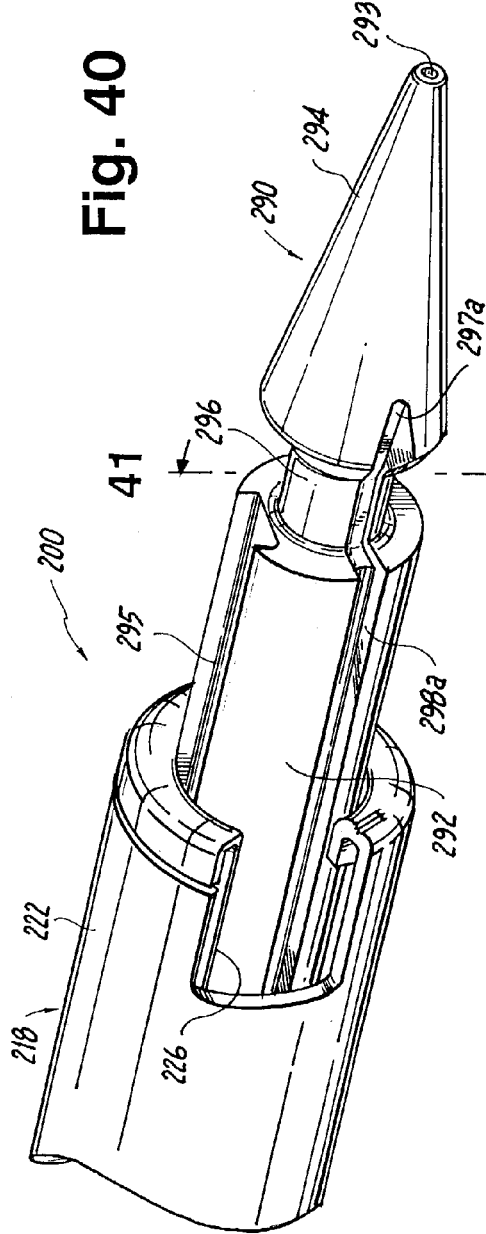
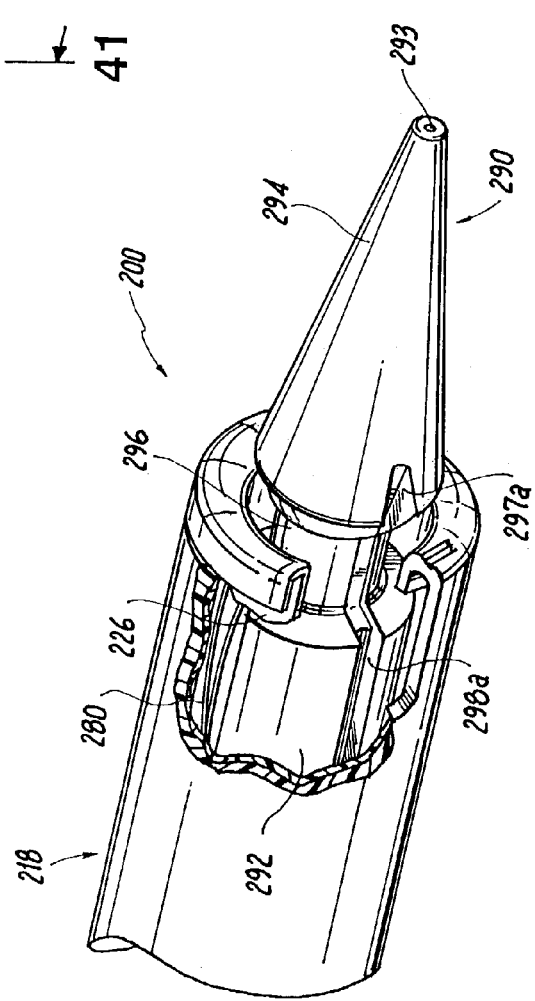
Fig. 40
Fig. 41
Fig. 42

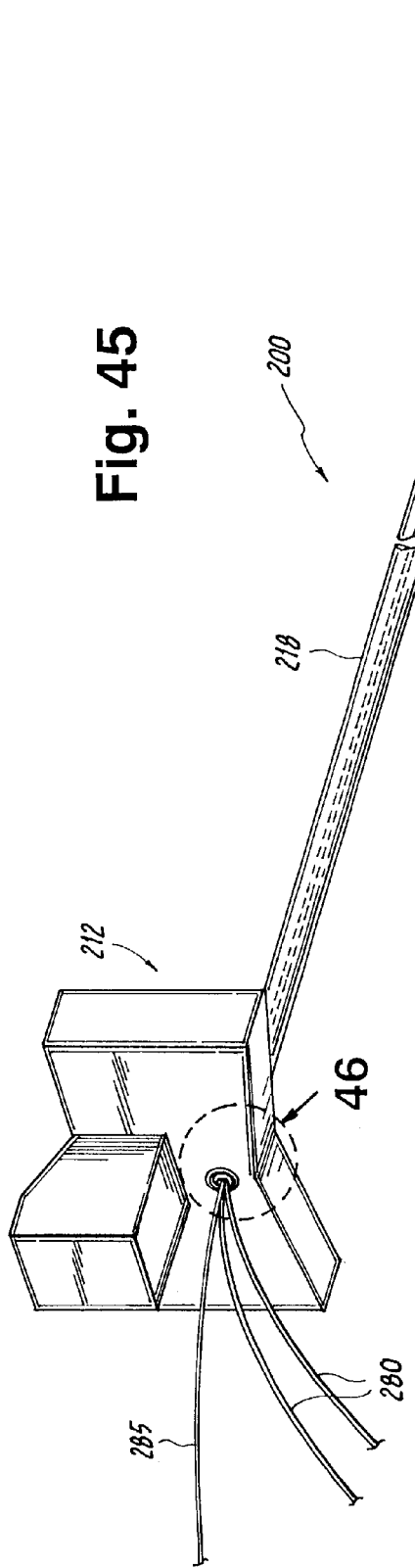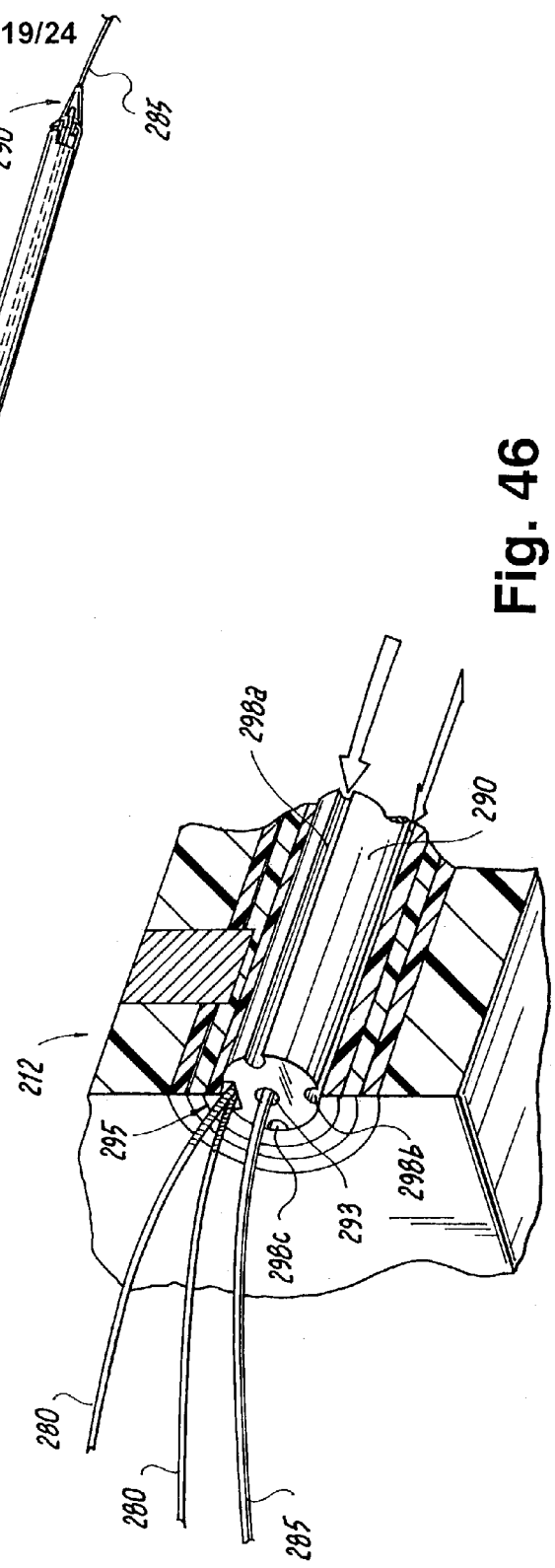

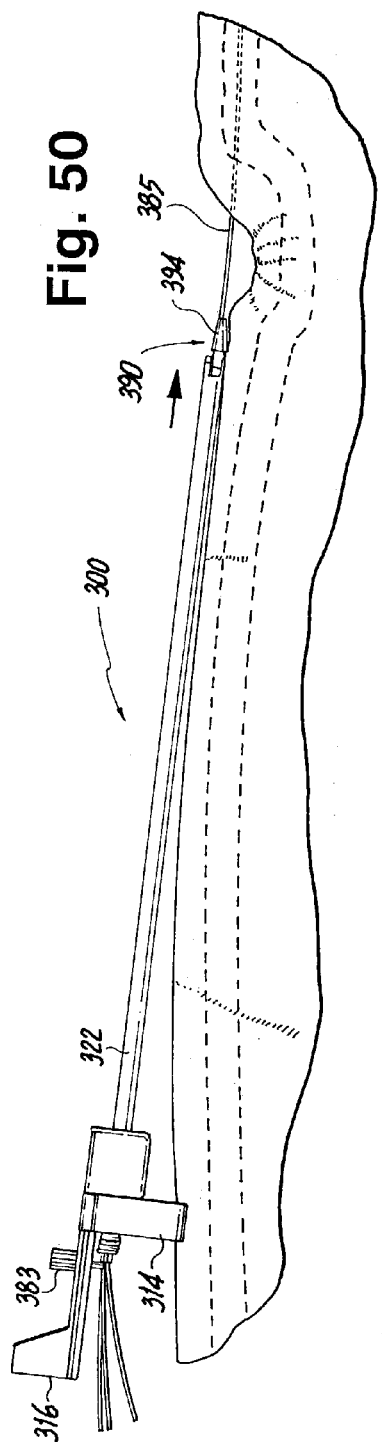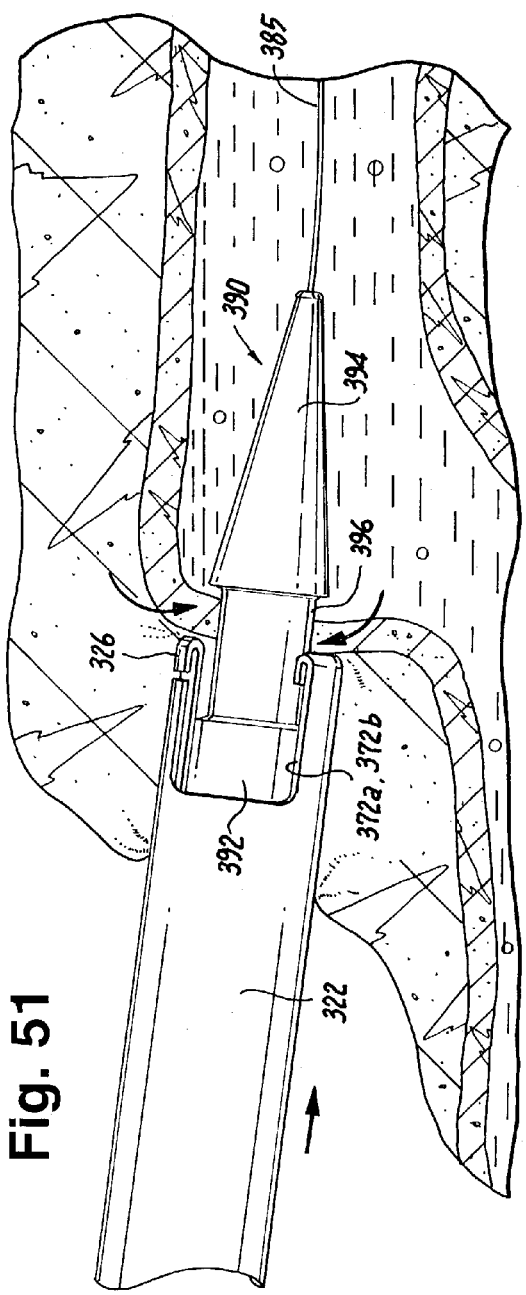

APPARATUS FOR SUTURING A BLOOD VESSEL

CROSS-REFERENCE TO RELATED APPLICATIONS

The subject application is a continuation-in-part of U.S. patent application Ser. No. 10/252,808, filed Sep. 23, 2002 now U.S. Pat. No. 7,041,119, which is a continuation-in-part of U.S. patent application Ser. No. 09/794,553, filed Feb. 27, 2001, now U.S. Pat. No. 6,454,777.

BACKGROUND OF THE INVENTION

1. Field of the Invention

The subject invention is directed to an apparatus and method for closing incisions in blood vessels, and more particularly, to an apparatus and method for percutaneously applying a suture to the wall of a blood vessel to close a surgical incision formed therein.

2. Background of the Related Art

Surgical procedures requiring the introduction of a catheter into a blood vessel, such as the femoral or iliac artery, are well known in the art. Such procedures involve piercing the wall of the blood vessel, inserting an introducer sheath into the opening in the blood vessel, and maneuvering the catheter through the sheath to a target site within the blood vessel. At the conclusion of the procedure, it is necessary to seal the puncture wound in the wall of the blood vessel. It is common to accomplish this by applying direct pressure to the puncture site until homeostasis is achieved. This technique is time consuming, uncomfortable and can cause thrombosis, thereby presenting a danger to the patient.

Consequently, surgical instruments have been developed for suturing a puncture wound in a blood vessel, examples of which are disclosed in U.S. Pat. No. 5,746,755 to Wood et al., U.S. Pat. No. 5,836,955 to Beulna et al., U.S. Pat. No. 5,921,994 to Andreas et al., and U.S. Pat. No. 5,980,539 to Kontos. While these instruments provide improvements over common compression techniques, they remain difficult to use and unable to accomplish the desired task within a relatively short amount of time.

Therefore, it would be beneficial to provide an apparatus and method for suturing a puncture wound in the wall of a blood vessel in a relatively short amount of time and with relative ease.

SUMMARY OF THE INVENTION

The subject invention is directed to a new and useful apparatus for percutaneously applying sutures, and more particularly, to an apparatus for closing an incision in the wall of a blood vessel in a relatively short amount of time and with relative ease as compared to prior art devices of its type.

The subject apparatus includes an elongated tubular body defining opposed proximal and distal end portions and having a longitudinal axis extending therethrough. The body includes an inner tubular member, an outer tubular member and a central tubular member disposed between the inner and outer tubular members. The inner tubular member and the central tubular member are mounted for movement relative to the outer tubular member about the longitudinal axis of the body.

The inner tubular member has an arcuate needle carrying channel formed at the distal end thereof for carrying a pair of arcuate suture needles in back-to-back orientation within a plane extending generally perpendicular to the longitudinal axis of the body. The central tubular member has a distal driving stem extending into the arcuate channel of the inner tubular member and positioned between the pair of suture needles for sequentially driving the suture needles from the arcuate channel of the inner tubular member upon rotation of the central tubular member relative to the inner tubular member. The outer tubular member has a pair of diametrically opposed tissue reception areas formed in the distal end of the tube wall. An arcuate needle reception channel is also formed at the distal end of the outer tubular member for receiving the pair of arcuate suture needles after the suture needles have been sequentially driven from the arcuate channel of the inner tubular member by the driving stem of the central tubular member, through tissue gathered in the tissue reception areas.

The apparatus further a vascular dilator having an elongated body portion and a tapered distal tip portion. The elongated body portion is slidably disposed within the inner tubular member and has an annular groove formed therein adjacent to the distal tip portion. The distal tip portion extends beyond the distal end of the inner tubular member for positioning the suturing device at an incision in the wall of a blood vessel. The dilator is mounted for movement between an extended position in which the annular groove is exposed allowing tissue to prolapse therein so as to provide tactile feedback and a retracted position in which the prolapsed tissue within the annular groove is urged in a proximal direction and gathered within the tissue receiving recesses of the outer tubular member.

Preferably, the suturing apparatus includes a handle portion that is operatively associated the proximal end portion of the outer tubular member, the central tubular member and the inner tubular member for co-axially supporting the outer tubular member, the central tubular member and the inner tubular member.

It is envisioned that the suturing apparatus includes a mechanism for biasing the dilator in the retracted position and a device for securing the dilator in the extended position. In a preferred embodiment, the mechanism for biasing the dilator in the retracted position includes a spring element, for example, a helical spring or a leaf spring which is engaged with the proximal end of the dilator. The device for securing the dilator in the extended position preferably includes a pin which inserted into a hole formed in the handle portion and engages with the proximal end of the dilator so as to prevent axial movement of the dilator. Preferrably, the securing pin is adapted and configured for preventing rotation of the inner tubular member and the central tubular member relative to the outer tubular member.

It is further envisioned that an actuator is operatively associated with the handle portion for effectuating the relative movement of the inner tubular member and the central tubular member relative to the outer tubular member so as to cause sequential passing of the suture needles from the arcuate channel of the inner tubular member to the arcuate channel of the outer tubular member. Preferably, means are formed within the needle receiving channel of the outer tubular member for securely retaining the suture needles therein, and tissue gripping features are formed on exterior distal surfaces of the outer tubular member.

In accordance with a preferred embodiment of the subject invention, the inner tubular member, the central tubular member and the outer tubular member include cooperating overlying cam slots, and a cam pin extends through the overlying cooperating cam slots to cause the inner tubular member and the central tubular member to rotate relative to the outer tubular member. In addition, a proximal retaining pin is operatively associated with a proximal portion of the elongated tubular body for maintaining the relative axial positions of the outer tubular member, the central tubular inner tubular member and the inner tubular member. The cam pin is operatively connected to the actuator, the actuator is mounted for movement relative to a handle member, and the retaining pin is operatively connected to the handle member.

The subject invention is also directed to a method of suturing the wall of a blood vessel which includes the steps of positioning an elongated tubular body having a longitudinal axis extending therethrough adjacent an incision in the wall of a blood vessel, with the body including a first tubular member and a second tubular member, the first tubular member mounted for movement relative to the second tubular member about the longitudinal axis of the tubular body, and carrying first and second suture needles connected to one another by an elongated suture. The method further includes the sequential steps of passing the first suture needle from the first tubular member, through the wall of the blood vessel, to the second tubular member, and then subsequently passing the second suture needle from the first tubular member, through the wall of the blood vessel, to the second tubular member. The method further includes the steps of withdrawing the elongated tubular body from the wall of the blood vessel, and then tying a knot in the suture to close the incision in the wall of the blood vessel.

The subject invention is further directed to a suturing device that includes an inner tubular member having an arcuate channel formed at a distal end thereof for carrying a pair of arcuate suture needles in back-to-back orientation, a central tubular member having a distal driving stem extending into the channel of the inner tubular member and positioned between the pair of suture needles for sequentially driving the suture needles from the channel of the inner tubular member upon rotation of the central tubular member relative to the inner tubular member, and an outer tubular member having a channel formed at a distal end thereof for receiving the pair of arcuate suture needles after the suture needles have been sequentially driven from the arcuate channel of the inner tubular member by the driving stem of the central tubular member.

In addition, the device includes a vascular dilator having an elongated body portion disposed within the inner tubular member and a tapered distal tip portion dimensioned to extend beyond the distal end of the inner tubular member for introducing the suturing device into a blood vessel. The vascular dilator is slidably disposed within the inner tubular member and may have a central lumen extending therethrough to accommodate a guidewire. An annular groove is formed between the tapered distal tip portion of the dilator and the elongated body portion of the dilator. This groove will provide a tactile indication to a surgeon as the wall of the blood vessel engages the groove when the device has reached its operating position.

Preferably, one or more elongated grooves are formed in an exterior surface of the elongated body of the vascular dilator for directing blood flow from the distal tip portion of the dilator to a location remote from the blood vessel for observation. This feature allows the surgeon or an assisting observer to determine whether the device is properly positioned for operation. The grooves direct blood flow to observation ports formed in the tubular body portion of the suturing device, or to a proximal end of the suturing device.

These and other aspects of the suturing apparatus and method of the subject invention and the method of using the same will become more readily apparent to those having ordinary skill in the art from the following detailed description of the invention taken in conjunction with the drawings described hereinbelow.

BRIEF DESCRIPTION OF THE DRAWINGS

So that those having ordinary skill in the art to which the subject invention pertains will more readily understand how to make and use the suturing apparatus of the subject invention, preferred embodiments thereof will be described in detail hereinbelow with reference to the drawings, wherein:

FIG. 1 is a perspective view of a vascular suturing device constructed in accordance with a preferred embodiment of the subject invention;

FIG. 2 is a top plan view of the vascular suturing device of FIG. 1;

FIG. 3 is a side elevational view of the vascular suturing device of FIG. 1;

FIG. 4 is an exploded perspective view of the vascular suturing device of FIG. 1 with parts separated for ease of illustration;

FIG. 5 is an enlarged localized perspective view of the distal end portion of the vascular suturing device of FIG. 1;

FIG. 6 is a cross-sectional view of the vascular suturing device taken along line 6—6 of FIG. 5;

FIG. 7 is a cross-sectional view of the vascular suturing device taken along line 7—7 of FIG. 1;

FIG. 8 is a cross-sectional view of the vascular suturing device taken along line 8—8 of FIG. 1;

FIG. 9 is a top plan view of the outer tubular member of the vascular suturing device of FIG. 1 illustrating the elongated cam slot defined therein and the arcuate needle receiving channel formed at the distal end thereof;

FIG. 10 is an enlarged side elevational view of the distal end portion of the outer tubular member of FIG. 9 as viewed along line 10—10 of FIG. 9;

FIG. 11 is an enlarged front elevational view of the distal end portion of the outer tubular member of FIG. 9 as viewed along line 11—11 of FIG. 9;

FIG. 12 is a top plan view of the central tubular member of the vascular suturing device of FIG. 1 illustrating the stepped cam slot defined therein and the needle driving stem formed at the distal end thereof;

FIG. 13 is an enlarged cross-sectional view of the central tubular member of FIG. 12 taken along line 13—13 of FIG. 12;

FIG. 14 is an enlarged front elevational view of the distal end portion of the central tubular member of FIG. 12 as viewed along line 14—14 of FIG. 12;

FIG. 22 is a top plan view of the vascular suturing device of the subject invention as viewed along line 22—22 of FIG. 20 illustrating the initial position of the cam pin within the cam slots of the tubular members;

FIG. 23 is an enlarged front elevational view of the distal end of the vascular suturing device of the subject invention as viewed along line 23—23 of FIG. 20 illustrating the initial back-to-back orientation of the suturing needles disposed in the arcuate needle carrying channel of the inner tubular member;

FIG. 24 is a top plan view of the vascular suturing device of the subject invention as viewed along line 22—22 of FIG. 20 illustrating a second position of the cam pin within the cam slots of the tubular members;

FIG. 25 is an enlarged front elevational view of the distal end of the vascular suturing device of the subject invention as viewed along line 23—23 of FIG. 20 when the inner tubular member rotates in a counter clock-wise direction relative to the outer tubular member so as to clamp the wall of the blood vessel between grasping surfaces of the inner and outer tubular members;

FIG. 26 is a top plan view of the vascular suturing device of the subject invention as viewed along line 22—22 of FIG. 20 illustrating a third position of the cam pin within the cam slots of the tubular members;

FIG. 27 is an enlarged front elevational view of the distal end of the vascular suturing device of the subject invention as viewed along line 23—23 of FIG. 20 when the first suturing needle is driven from the needle carrying channel of the inner tubular member by the needle driving stem of the central tubular member, through the clamped blood vessel wall and into the needle receiving channel of the outer tubular member;

FIG. 28 is a top plan view of the vascular suturing device of the subject invention as viewed along line 22—22 of FIG. 20 illustrating a fourth position of the cam pin within the cam slots of the tubular members;

FIG. 29 is an enlarged front elevational view of the distal end of the vascular suturing device of the subject invention as viewed along line 23—23 of FIG. 20 when the driving stem of the central tubular member and the inner tubular member are rotated in a clock-wise direction relative to the outer tubular member so as to position the driving stem behind the second suturing needle and to clamp the blood vessel wall between grasping surfaces of the inner and outer tubular members;

FIG. 30 is a top plan view of the vascular suturing device of the subject invention as viewed along line 22—22 of FIG. 20 illustrating a fifth position of the cam pin within the cam slots of the tubular members;

FIG. 31 is an enlarged front elevational view of the distal end of the vascular suturing device of the subject invention as viewed along line 23—23 of FIG. 20 when the second suturing needle is driven from the needle carrying channel of the inner tubular member by the needle driving stem of the central tubular member, through the clamped blood vessel wall and into the needle receiving channel of the outer tubular member;

FIG. 32 is a top plan view of the vascular suturing device of the subject invention as viewed along line 22—22 of FIG. 20 illustrating a sixth position of the cam pin within the cam slots of the tubular members;

FIG. 33 is an enlarged front elevational view of the distal end of the vascular suturing device of the subject invention as viewed along line 23—23 of FIG. 20 when the driving stem of the central tubular member and the inner tubular member are rotated in a counter clock-wise direction relative to the outer tubular member so as to release the clamped blood vessel wall;

FIG. 38 illustrates the percutaneous introduction of the vascular suturing device of FIG. 35 to the incision site of the blood vessel along a path defined by a guidewire extending through a central bore formed in the vascular introducer;

FIG. 39 illustrates the distal end portion of the vascular suturing device of FIG. 35 with the vascular introducer extending through the incision in the wall of a blood vessel, such that the wall of the blood vessel protrudes into a cavity formed in the vascular introducer to provide a tactile indication to the surgeon to confirm the location of the device;

FIG. 40 is a perspective view of the distal end portion of yet another vascular suturing device constructed in accordance with a preferred embodiment of the subject invention which includes an integral vascular introducer configured to allow visual observation of arterial blood flow to confirm the location of the device, with the vascular introducer separated from the instrument for ease of illustration;

FIG. 41 is a cross-sectional view taken along line 41—41 of FIG. 40 illustrating;

FIG. 42 is a perspective view of the distal end portion of the vascular suturing device of FIG. 40 illustrating the pathway for arterial blood flow;

FIG. 45 is a perspective view of a variant of the vascular suturing device of FIG. 40, wherein the blood observation ports are provided at the rear end of the device;

FIG. 46 is an enlarged localized perspective view of the rear end portion of the device illustrating the channels formed in the proximal end portion of the vascular introducer which, in this embodiment, extends through the entirety of the tubular body portion of the device;

FIG. 50 illustrates the percutaneous introduction of the vascular suturing device of FIG. 47 to the incision site of the blood vessel along a path defined by a guidewire extending through a central bore formed in the vascular introducer;

FIG. 51 illustrates the distal end portion of the vascular suturing device of FIG. 47 with the vascular introducer in the extended position and projecting through the incision in the wall of a blood vessel, such that the wall of the blood vessel protrudes into an annular cavity formed in the vascular introducer to provide a tactile indication to the surgeon to confirm the location of the device;

DETAILED DESCRIPTION OF PREFFERED EMBODIMENTS

Figure 15:
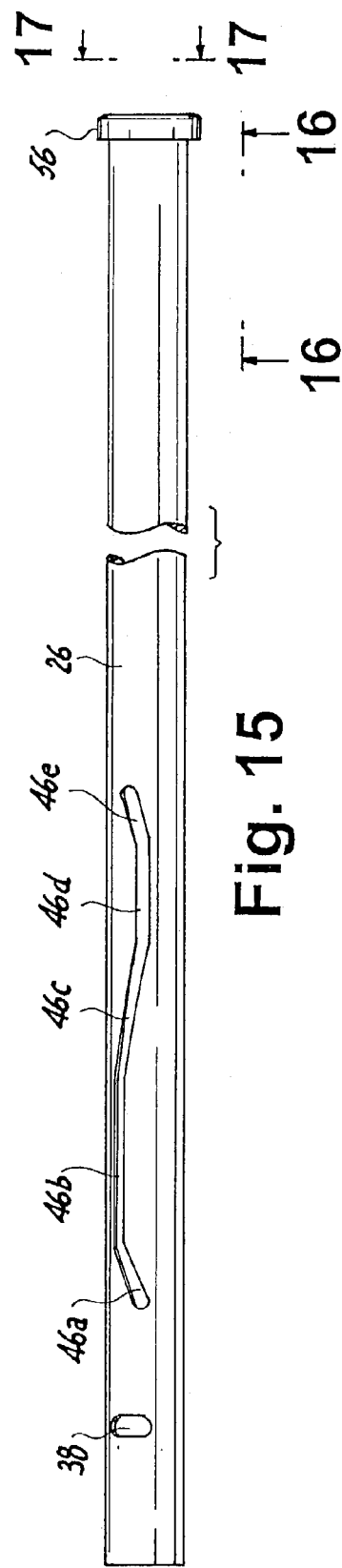
FIG. 15 is a top plan view of the inner tubular member of the vascular suturing device of FIG. 1 illustrating the stepped cam slot defined therein and the arcuate needle carrying channel formed at the distal end thereof.

Referring now to the drawings wherein like reference numerals identify similar structural elements of the apparatus disclosed herein, there is illustrated in FIG. 1 a vascular suturing device constructed in accordance with a preferred embodiment of the subject invention and designated generally by reference numeral 10. In the specification that follows the term "distal" shall refer to the end of the vascular suturing device that is nearest to the surgical site, while the term "proximal" shall refer to the end of the vascular suturing device that is farthest from the surgical site.

Referring now to FIGS. 1–3, 7 and 8, vascular suturing device 10 includes a proximal handle portion 12 having a stationary support portion 14 and a translating actuation portion 16. The components of handle portion 12 are preferably formed from a high strength thermoplastic material such as, for example, Lexan®. Support portion 14 is ergonomically configured to be positioned on a patient's leg during a vascular closure procedure. An elongated tubular body portion 18 extends from a bore 15 in support portion 14, through an elongate passage 17 in actuation portion 16, and includes a distal suture applying portion 20, which is shown specifically in the localized view of FIG. 5. It is envisioned that the distal suture applying portion could be constructed as a replaceable cartridge configured for mounting at the distal end of the body portion.

Body portion 18 has three relatively movable concentric tubular members which are illustrated in FIG. 4 in an unassembled condition. These members include an outer tubular member 22, an inner tubular 26 and a central tubular member 24 disposed between the inner and outer tubular members 22 and 26. One or more of the tubular components of body portion 18 are preferably formed from stainless steel, or a similar bio-compatible material.

As best seen in FIGS. 3 and 7, a proximal positioning pin 28 extends through a countersunk transverse bore 30 in support portion 14 for engaging an aperture 34 in the proximal end portion of outer tubular member 22 (see FIG. 9). Positioning pin 28 also engages a relatively large arcuate slot 36 in the proximal potion of central tubular member 24 (see FIGS. 12 and 13), and a relatively small arcuate slot 38 in the proximal portion of inner tubular member 26 (see FIG. 15). Proximal positioning pin 28 is adapted and configured to maintain the relative axial positions of the three tubular members.

As best seen in FIGS. 3 and 8, a distal cam pin 40 extends through a countersunk transverse bore 45 in actuation portion 16 for engaging a linear cam slot 42 formed in outer tubular member 22 (see FIG. 9). Cam pin 40 also engages a first stepped cam slot 44 in central tubular member 24 (see FIG. 12), and a second stepped cam slot 46 is inner tubular member 26 (see FIG. 15). Distal cam pin 40 is adapted and configured to effectuate the relative axial rotation of the three concentric tubular members of body portion 18 as it translates in a distal direction through the cooperating superimposed, overlying cam slots 42, 44 and 46, of tubular members 22, 24 and 26, respectively, under the guidance of the translating actuation portion 16.

Figure 17:
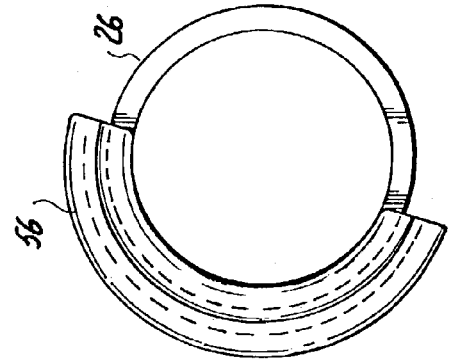
FIG. 17 is an enlarged front elevational view of the distal end portion of the inner tubular member of FIG. 15 as viewed along line 17—17 of FIG. 15.

Referring now to FIGS. 4 and 5, the distal suture applying portion 20 of suturing apparatus 10 is defined in part by a U-shaped annular channel 52 formed at the distal end of outer tubular member 22 (see FIG. 11), and in part by a U-shaped annular channel 56 formed at the distal end of inner tubular member 26 (see FIG. 17). As discussed in greater detail hereinbelow, the arcuate channel 56 of inner tubular member 26 defines a needle carrying channel for carrying a pair of curved suture needles 50a and 50b disposed in back-to-back orientation in a plane extending perpendicular to the longitudinal axis of the tubular body portion 18. The arcuate channel 52 of outer tubular member defines a needle receiving channel for receiving suture needles 50a and 50b after they have been sequentially driven through the wall of a blood vessel during a vascular suturing procedure.

As best seen in FIG. 5, a depending distal wall portion 62 of outer tubular member 22 (see FIG. 10) abuts the upturned wall of needle carrying channel 56 to enclose the curved suture needles therein. In addition, FIG. 5 illustrates the position of the distal driving stem 54 of central tubular member 22 (see FIG. 14) which extends into the needle carrying channel 56 of inner tubular member 26 between the adjacent rear ends of the suture needles 50a and 50b for sequentially driving the suture needles therefrom during a vascular suturing procedure. FIG. 5 also illustrates the diametrically opposed tissue reception areas 60a and 60b that are formed at the distal end of body portion 18 for receiving or gathering-up the wall of a blood vessel. In addition, as illustrated in FIGS. 5 and 6, the terminal radial edges of arcuate channels 52 and 56 are provided with ridged or textured gripping surfaces 57 that extend generally perpendicular to the edges of the channels for gripping the wall of a blood vessel during a suturing procedure.

Figure 16:
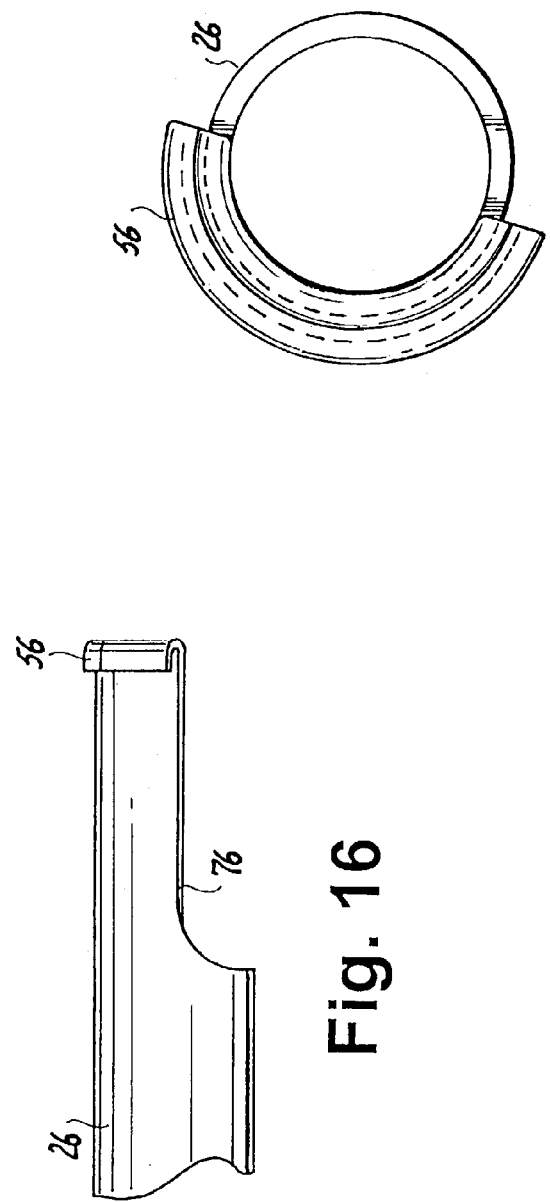
FIG. 16 is an enlarged side-elevational view of the distal end portion of the inner tubular member of FIG. 15 as viewed along line 16—16 of FIG. 15.

Referring now to FIG. 4, the relatively movable concentric tubular members of body portion 18 are uniquely configured to operate in conjunction with one another during a vascular suturing procedure. In particular, the outer tubular member 22 has a uniform cross-sectional configuration along its length, as does the inner tubular member 26. In contrast, as shown in FIG. 12, the central tubular member 24 is partially tapered or truncated along a portion of its length so as to accommodate the structural features of the inner tubular member 26 as it is received therein. As best seen in FIG. 10, the distal end portion of outer tubular member 22 has diametrically opposed recesses 72a and 72b which define part of the tissue reception areas 60a and 60b shown in FIG. 5. Similarly, FIG. 16 illustrates an undercut 76 formed at the distal end of inner tubular member 26 which also defines part of the tissue engagement areas 60a and 60b.

FIG. 4 also illustrates the suture 80 that extends between the two curved suture needles 50a and 50b disposed within needle carrying channel 56. Suture 80 may be of braided or monofilament construction, and can be absorbable or non-absorbable. It is normally stored within the space defined by the truncated area of central tubular member 24, and can extend to the exterior of the instrument through an aperture (not shown) formed in tubular body 18 such that the free ends thereof are easily accessible by the surgeon.

Referring now to FIG. 9, as noted above, the outer tubular member 22 has a linear cam slot 42 for cooperating with cam pin 40 and an aperture 34 for receiving positioning pin 28. Consequently, axial movement of actuator 16 during a suturing procedure does not cause any rotational movement of outer tubular member 22. In contrast, referring to FIG. 15, inner tubular member 26 has a stepped cam slot 46 for cooperating with cam pin 40 and a relatively short arcuate slot 38 for accommodating positioning pin 28. Cam slot 46 has four inflection points defining five distinct slot sections for effectuating the rotational movement of inner tubular member 26 relative to the outer tubular member 22, and more particularly, for sequentially approximating circumferentially adjacent terminal ends of the arcuate channels 52 and 56 of the outer and inner tubular members 22 and 26 so as to clamp portions of the wall of a punctured blood vessel therebetween.

In particular, cam slot 46 has a first helical section 46a that facilitates rotational movement of the inner tubular member 26 in a first direction through a first angle of rotation; a first linear section 46b corresponding to a first dwell period in which the inner tubular member 26 does not rotate about its axis; a second helical section 46c that facilitates rotational movement of the inner tubular member 26 in a second direction through a second angle of rotation; a second linear section 46d corresponding to a second dwell period in which the inner tubular member 26 does not rotate about its axis; and a third helical section 46e that facilitates rotational movement of the inner tubular member 26 in the first direction through a third angle of rotation.

Referring now to FIG. 12, the central tubular member 24 has a stepped cam slot 44 for cooperating with cam pin 40 and a relatively long arcuate slot 36 for accommodating positioning pin 28. Cam slot 44 has two inflection points defining three distinct slot sections for effectuating the rotational movement of inner tubular member 24 relative to the outer tubular member 22, and more particularly, for sequentially driving the curved suture needles 50a and 50b from needle carrying channel 56 of inner tubular member 26.

In particular, cam slot 44 has a first helical section 44a that facilitates rotational movement of the central tubular member 24 in a first direction through a first angle of rotation during which the driving stem 54 drives a first curved suture needle from needle carrying channel 56; a second helical section 44b that facilitates rotational movement of the central tubular member 24 in a second direction through a second angle of rotation during which the driving stem 54 drives a second curved suture needle from needle carrying channel 56; and a third helical section 44c that facilitates rotational movement of the central tubular member 24 in the first direction through a third angle of rotation to reposition the driving stem 54 of central tubular member 44 in a neutral position within needle carrying channel 56 of inner tubular member 26.

As discussed in detail hereinbelow with respect to FIGS. 20 through 34, the rotational movements of the central and inner tubular members 24 and 26, and the dwell periods of the inner tubular member 26 effectuated by the translation of the cam pin 40 through the cooperating superimposed cam slots 44 and 46 correspond to sequential steps in the suturing methodology of the subject invention.

Figure 18:
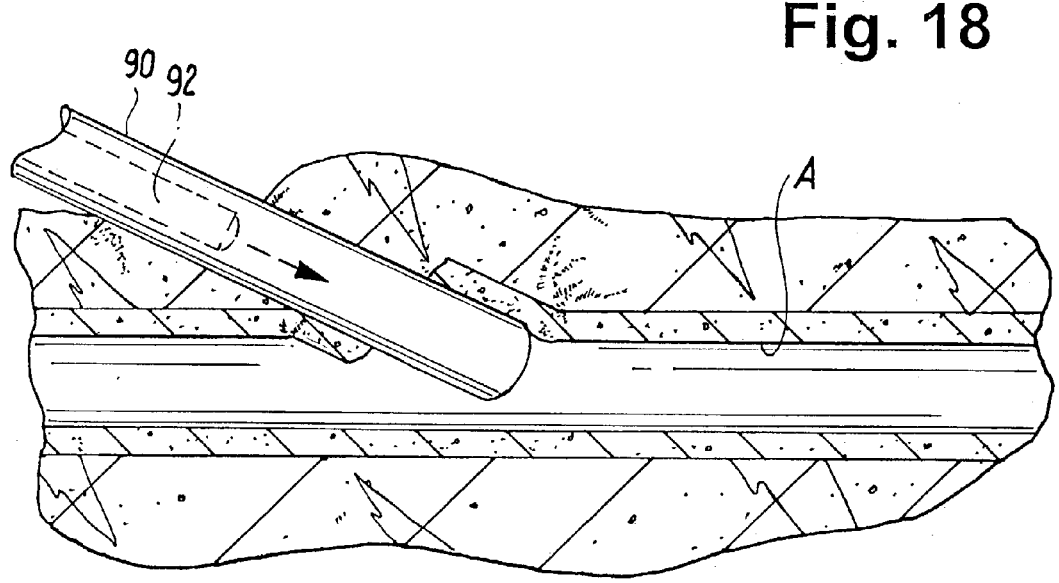
FIG. 18 illustrates a tubular cannula extended through an incision in the wall of a blood vessel, as a flexible stylet is introduced therethrough.
Figure 19:
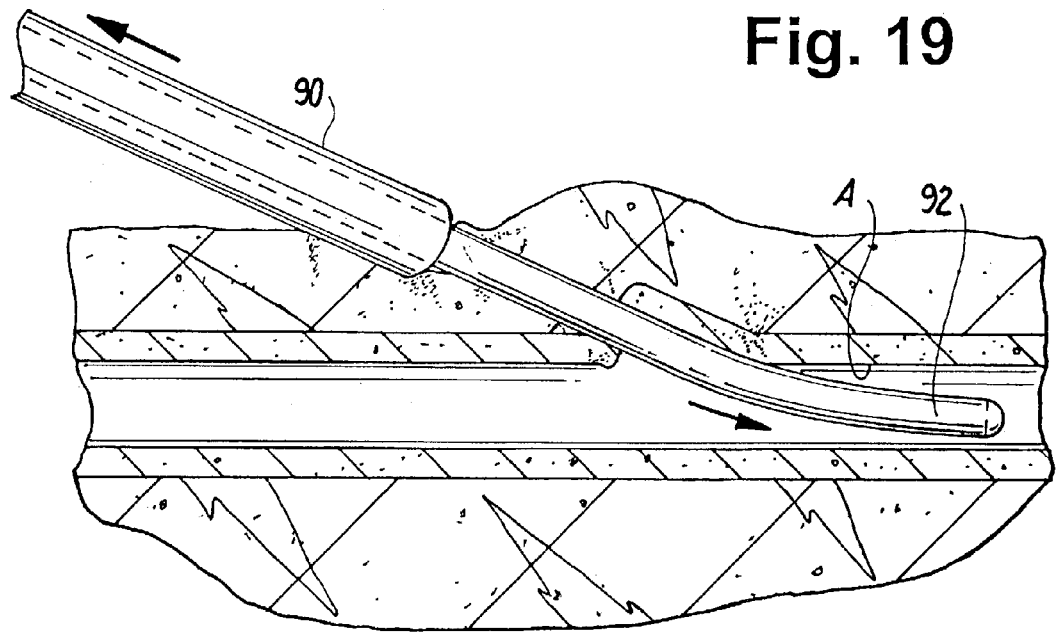
FIG. 19 illustrates a flexible stylet extended into the blood vessel as the tubular cannula is removed from the incision site.
Figure 20:
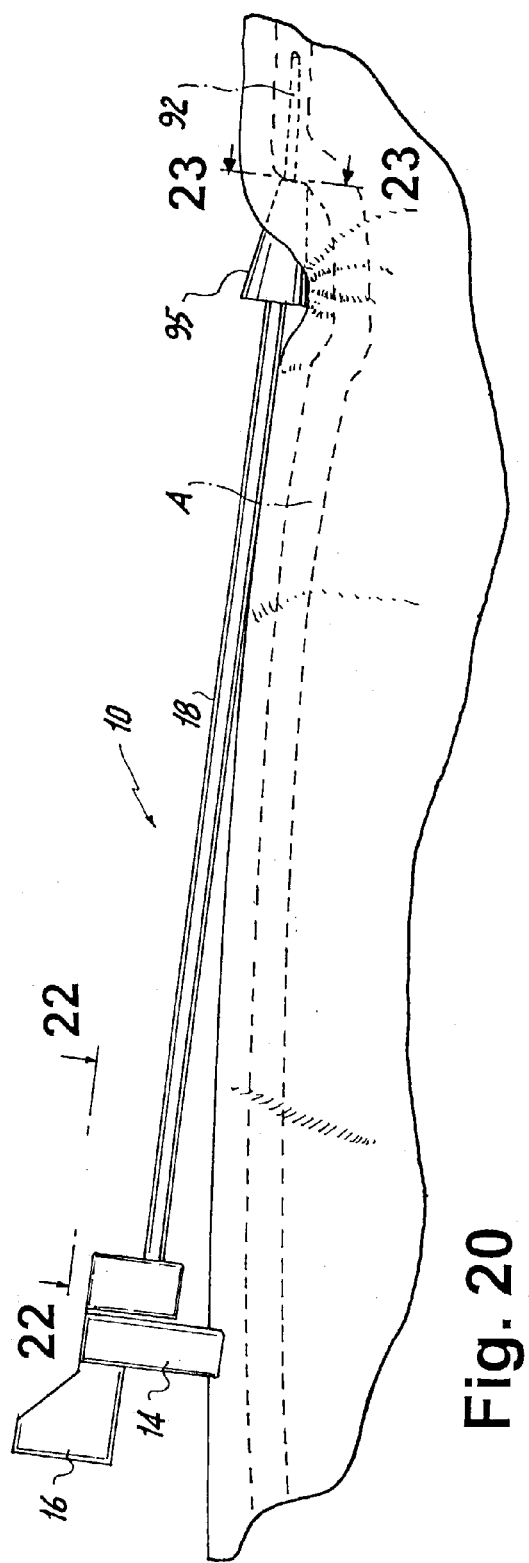
FIG. 20 illustrates the percutaneous introduction of the vascular suturing device of the subject invention to the incision site of the blood vessel along the path of the stylet positioned in FIG. 19.
Figure 21:
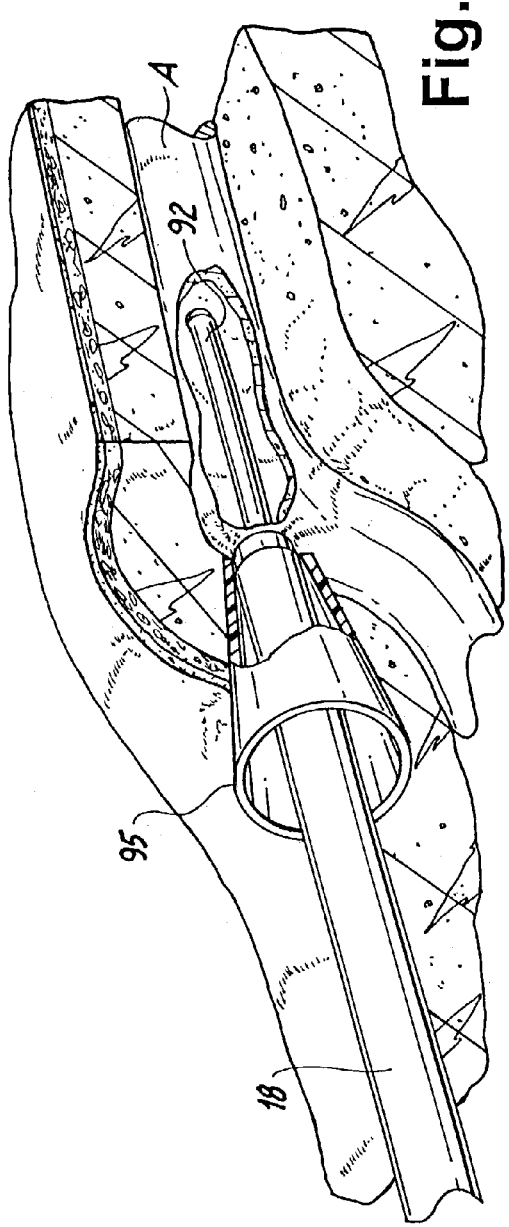
FIG. 21 is an enlarged partial cross-sectional view of the distal portion of the vascular suturing device of the subject invention with the wall of the blood vessel engaged thereby.

In use, at the conclusion of a surgical procedure conducted through an incision or puncture wound in the wall of a blood vessel, such as the femoral artery, a tubular cannula 90 is utilized to facilitate the percutaneous introduction of a flexible stylet 92 into the lumen of the blood vessel A, as illustrated in FIG. 18. Thereafter, as shown in FIG. 19, the tubular cannula 90 is removed from the incision site. Then, the vascular suturing device 10 of the subject invention, with the aide of an optional tapered nose piece 95, is percutaneously introduced to the surgical site as it is guided along the stylet by way of the central lumen of body portion 18, as illustrated in FIGS. 20 and 21.

Referring to FIGS. 22 and 23, upon commencing the vascular suturing procedure of the subject invention, the cam pin 40 is in an initial position within the superimposed cam slots 42, 44 and 46 of tubular members 22, 24 and 26, respectively. This corresponds to the initial position of the suturing needles 50a and 50b within the arcuate needle carrying channel 56 of the inner tubular member 26, with the distal driving stem 54 of central tubular member 24 disposed therebetween.

Thereafter, when, through manipulation of actuation handle 16 relative to stationary handle portion 14, cam pin 40 is moved to the second position of FIG. 24, it has translated through the first helical section 46a of cam slot 46 in inner tubular member 26 to the first inflection point. This causes the inner tubular member 26 to rotate in a counter-clockwise direction relative to the outer tubular member 22 so as to clamp the wall of the blood vessel within engagement area 60a between grasping surfaces of the arcuate channels 52 and 56 of outer and inner tubular members 22 and 26, as shown in FIG. 25. At the same time, the cam pin 40 has traveled partially through the first helical section 44a of cam slot 44 in central member 24, so as to cause the central tubular member 24 follow the inner tubular member 26 in the counter-clockwise direction.

When the cam pin 40 is disposed in the third position of FIG. 26, it has traveled through the first linear section 46b of cam slot 46 in inner tubular member 26 to the second inflection point thereof, and through the remainder of the first helical section 44a of cam slot 44 in central tubular member 24 to the first inflection point thereof. This causes the inner tubular member 26 to remain stationary during the first dwell period, and causes the central tubular member 24 to continue to rotate in a counter-clockwise direction relative to the inner tubular member 26. Consequently, the first suturing needle 50a is driven from the needle carrying channel 56 of the inner tubular member 26 by the needle driving stem 54 of the central tubular member 24, through the clamped blood vessel wall and into the needle receiving channel 52 of the outer tubular member 22, where it is captured by a retention structure 55a, such as a protuberance depending from the wall of channel 52, as shown in FIG. 27.

Later, when the cam pin 40 is disposed in the fourth position of FIG. 28, it has traveled through the second helical section 46c of cam slot 46 of inner tubular member 26 to the third inflection point thereof, and partially through the second helical section 44b of cam slot 44 in central tubular member 24. This causes, the inner tubular member 26 to rotate in a clockwise direction relative to the outer tubular member 22 so as to clamp the blood vessel wall within tissue engagement area 60b between adjacent grasping surfaces of the outer and inner tubular members 22 and 26, as shown in FIG. 29. At the same time, the central tubular member 26 rotates in a clockwise direction so as to move into a driving position behind the second curved suturing needle 50b in needle carrying channel 56 of inner tubular member 26.

Thereafter, when the cam pin 40 is disposed in the fifth position of FIG. 30, it has traveled through the second linear section 46d of cam slot 46 of inner tubular member 26 to the fourth inflection point thereof, and through the reminder of the second helical section 44b of central tubular member 24. This causes the inner tubular member 26 to remain stationary during the second dwell period, while the central tubular member 24 continues to rotate in a clockwise direction such the distal driving stem 54 drives the second suturing needle 50b from the needle carrying channel 56 of the inner tubular member 26, through the clamped blood vessel wall and into the needle receiving channel 52 of the outer tubular member 22, where it is captured by retention structure 55b, as shown in FIG. 31. Although the retention structures 55a and 55b are shown as protuberances, other structures may be provided to retain the suture needles. For example, the width of the channel could gradually reduce in size to capture the suture needles.

When the cam pin 40 is in the sixth position of FIG. 32, it has traveled completely through the linear cam slot 42 of outer tubular member 22, through the third helical section 46e of cam slot 46 of inner tubular member 26, and through the third helical section 44c of cam slot 44 in central tubular member 24. This causes the inner tubular member 26 to rotate in a counter-clockwise direction to release the wall of the blood vessel and causes the central tubular member 24 to rotate in a counter clockwise direction so as to move the distal driving stem 54 into a neutral position within the needle carrying channel 56 of inner tubular member 26, as shown in FIG. 33.

Figure 34:
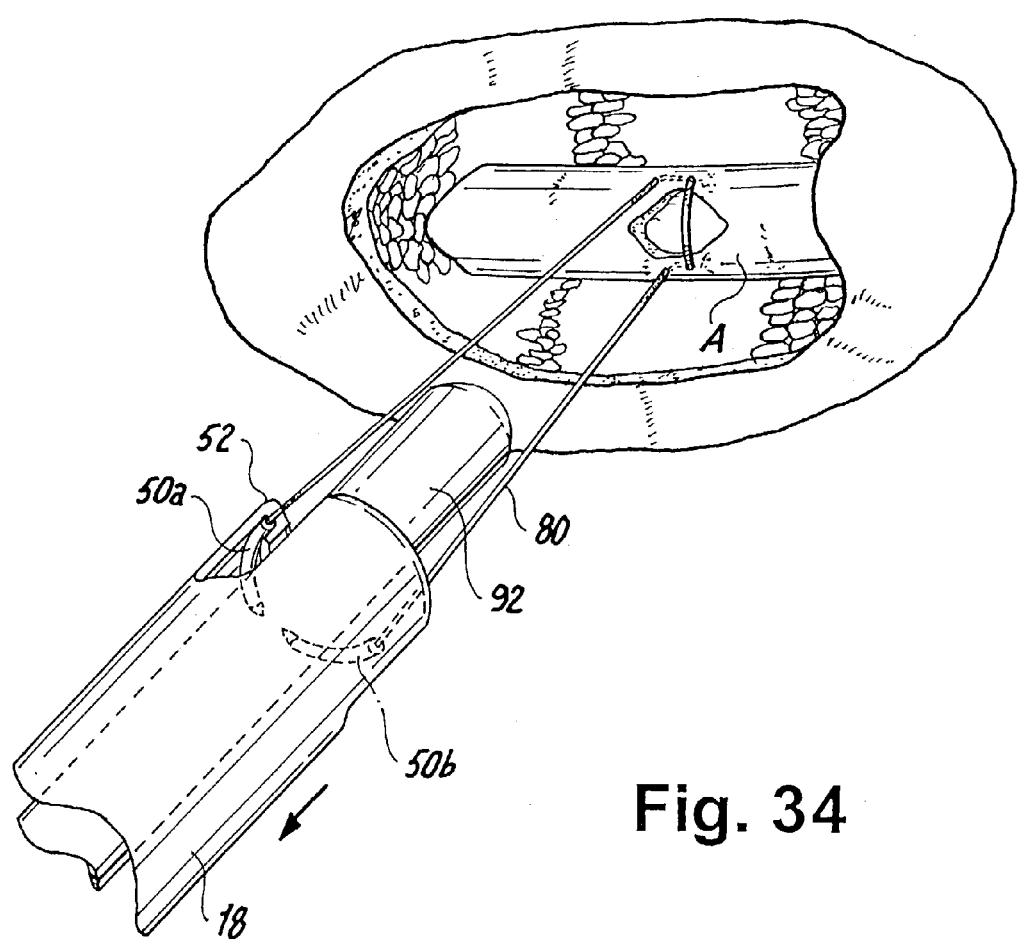
FIG. 34 illustrates the removal of the vascular suturing device of the subject invention as it is withdrawn from the incision site carrying the suturing needles therewith.

Referring now to FIG. 34, at the conclusion of the needle driving sequence described hereinabove, the vascular suturing device 10 of the subject invention is withdrawn from the incision site carrying the captured suturing needles 50a and 50b therewith. Thereafter, the free ends of suture 80 are gathered by the surgeon and a knot is tied therein so as to close the puncture wound in the wall of the blood vessel.

Figure 35:
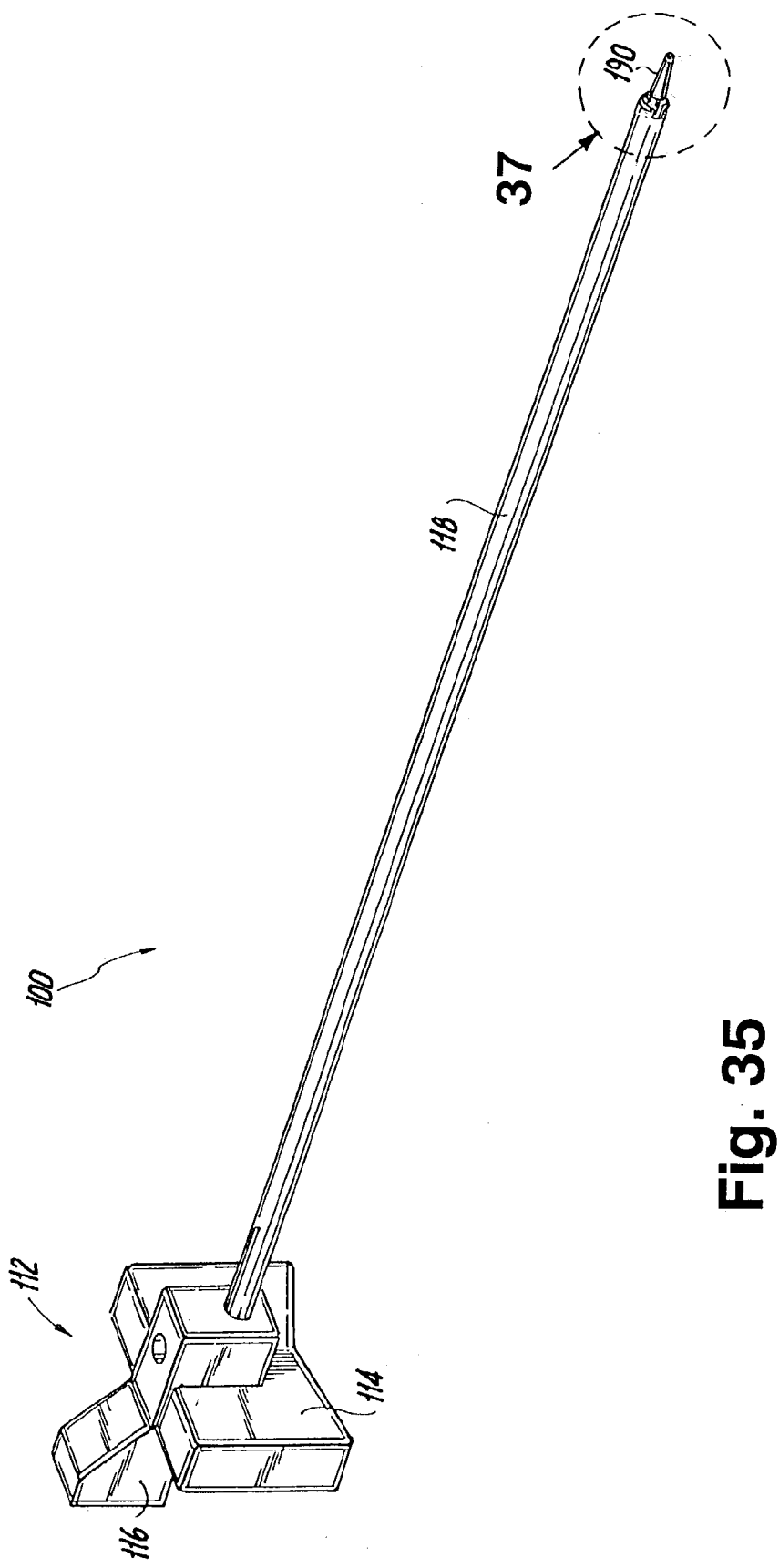
FIG. 35 is a perspective view of another vascular suturing device constructed in accordance with a preferred embodiment of the subject invention which includes an integral vascular introducer.
Figure 36:
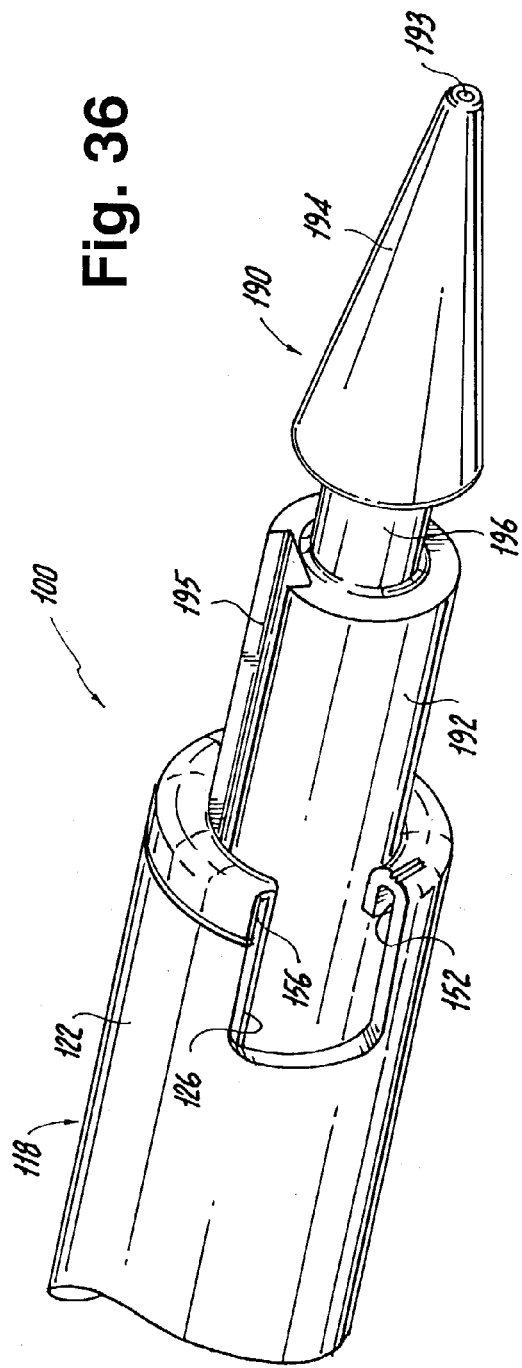
FIG. 36 is an enlarged perspective view of the distal end portion of the vascular suturing device of FIG. 35 with the vascular introducer separated from the instrument for ease of illustration.
Figure 37:
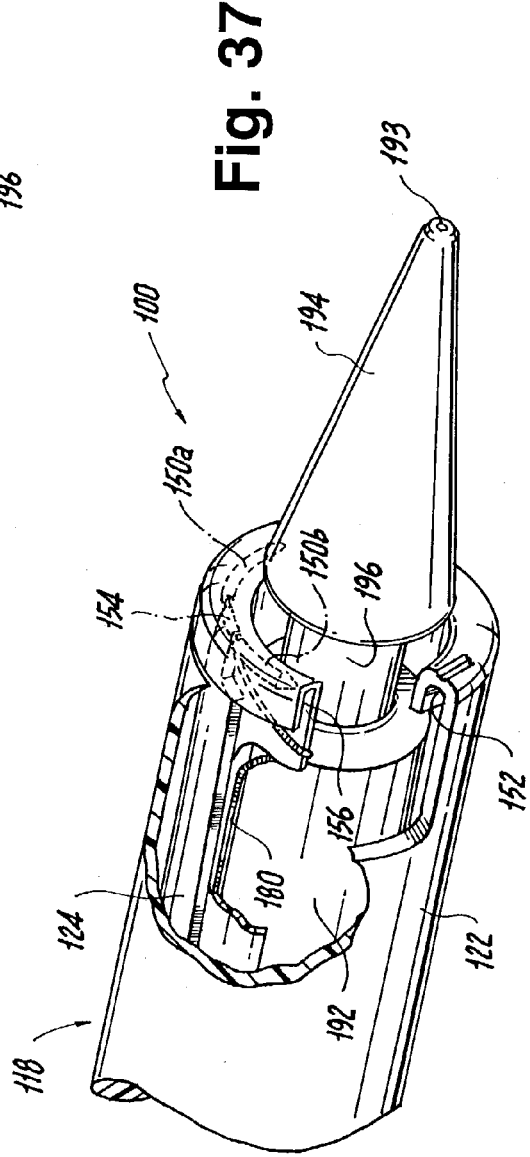
FIG. 37 is an enlarged perspective view of the distal end portion of the vascular suturing device of FIG. 35 with the walls of the tubular members broken away to reveal the vascular introducer disposed therein.

Referring to FIGS. 35 through 37, there is illustrated another vascular suturing device constructed in accordance with a preferred embodiment of the subject invention which is designated generally by reference numeral 100. Suturing device 100 is substantially similar to suturing device 10 in that it includes an outer tubular member 122, a central tubular member 124 and an inner tubular member 126. The inner tubular member 126 has an arcuate channel 156 formed at a distal end thereof for carrying a pair of arcuate suture needles in back-to-back orientation (see FIG. 37). The central tubular member 124 has a distal driving stem 154 extending into the channel of the inner tubular member 126 and positioned between the pair of suture needles for sequentially driving the suture needles from the channel of the inner tubular member 126 upon rotation of the central tubular member 124 relative to the inner tubular member 126. The outer tubular member 122 has an arcuate channel 152 formed at a distal end thereof for receiving the pair of arcuate suture needles after the suture needles have been sequentially driven from the arcuate channel of the inner tubular member 126 by the driving stem of the central tubular member 124.

As shown in FIG. 35, suturing device 100 also includes a handle portion 112 having a stationary handle 114 and an actuator 116 that is operatively associated with a proximal end portion of the outer tubular member 122, the central tubular member 124 and the inner tubular member 126. Actuator 116 effectuates the relative movement of the inner tubular member 126 and the central tubular member 124 relative to the outer tubular member 122 so as to cause sequential passing of the suture needles from the arcuate channel of the inner tubular member 126 to the arcuate channel of the outer tubular member 122. The relative movement of the tubular members is accomplished by cooperative overlying cam slots, and a cam pin that extends through the cooperative overlying cam slots to cause the inner tubular member and the central tubular member to rotate relative to the outer tubular member, as described hereinabove with respect to suturing device 10.

Suturing device 100 differs from suturing device 10 in that it includes an integral vascular dilator 190 that functions to guide the introduction of suturing device 100 through an incision in the wall of a blood vessel. Vascular dilator 190 is formed from the same or similar material as the other components of the suturing device and includes an elongated body portion 192 disposed within the central lumen of body portion 118, and more particularly, within the center bore of inner tubular member 126. Vascular dilator 190 further includes a tapered distal tip portion 194 dimensioned to extend beyond the distal end of the inner tubular member 126 for positioning the distal end of the suturing device at the incision in the wall of a blood vessel.

Vascular dilator 190 is preferably fixedly secured to the inner tubular member 126 of the suturing device 100 by way of a lock, pin, glue or other similar means. Vascular dilator 190 has a central lumen 193 extending therethrough to accommodate a guidewire 185, as illustrated in FIG. 38. In addition, the body portion 192 of dilator 190 is provided with an elongated storage channel 195 for accommodating the elongated suture 180 that is associated with the curved needles 150a, 150b, as best seen in FIG. 37. An annular groove 196 is formed between the tapered distal tip portion 194 of dilator 190 and the elongated body portion 192 of dilator 190. As illustrated in FIG. 39, annular groove 196 is configured and positioned to accept and become enveloped by the wall of the blood vessel. Consequently, the surgeon holding suturing device 100 will be provided with a tactile sensation, indicating that the suturing device 100 has reached its operating position against the wall of the blood vessel.

Referring now to FIGS. 40 through 42, there is illustrated another vascular suturing device constructed in accordance with a preferred embodiment of the subject invention which is designated generally by reference numeral 200. Suturing device 200 is substantially similar to suturing device 100 in that it includes an integral vascular dilator 290 having an elongated body portion 292 disposed within the central bore of inner tubular member 226 and a tapered distal tip portion 294 dimensioned to extend beyond the distal end of the inner tubular member 222. Dilator 290 also includes a guidewire bore 293 for guidewire 285, a suture storage channel 295 for suture 280 and an annular tissue envelopment groove 296 for tactile position indication, as described above with reference to FIG. 39.

Figure 44:
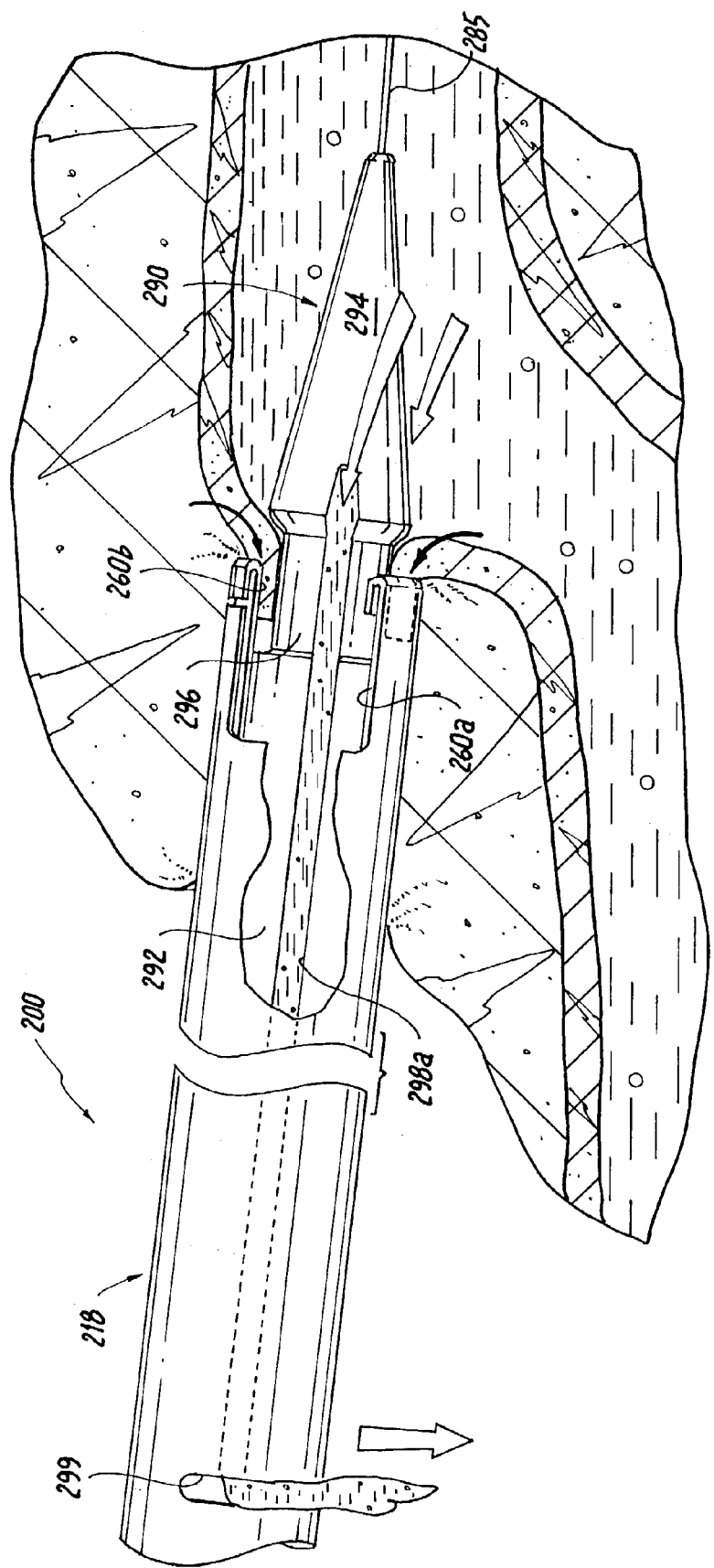
FIG. 44 illustrates the distal end portion of the vascular suturing device of FIG. 42, with the vascular introducer extending through the incision in the wall of a blood vessel to a location where the wall of the blood vessel protrudes into the tissue engagement areas and arterial blood flows through channels formed in the body of the introducer to ports in the device which to facilitate visual confirm of the location of the device at the incision site.

In addition, in suturing device 200, the vascular dilator 290 includes a system for providing the surgeon or an assisting observer with a visual indication that the device has reached its operating position at the incision site in the wall of the blood vessel to be sutured. The visual position indication system utilizes observable blood flow, and includes at least one but preferably three circumferentially spaced apart longitudinal grooves 298a–298c formed in the exterior surface of the body portion 292 of vascular dilator 290. The three longitudinal grooves extend from the annular groove 296 which communicates with correspondingly positioned and aligned inlet slots that are formed in the base of tapered distal portion 294 of dilator 290, of which inlet slot 297a is one that is shown. Grooves 298a–298c communicate with and deliver arterial/venous blood flow to corresponding observation port(s) 299 formed in the tubular body portion 218 of suturing device 200, remote form the incision site, as illustrated in FIG. 44. This feature or system allows the surgeon or an assisting observer to determine whether the distal end of suturing device 200 is properly positioned at the incision site for a suturing operation.

Figure 43:
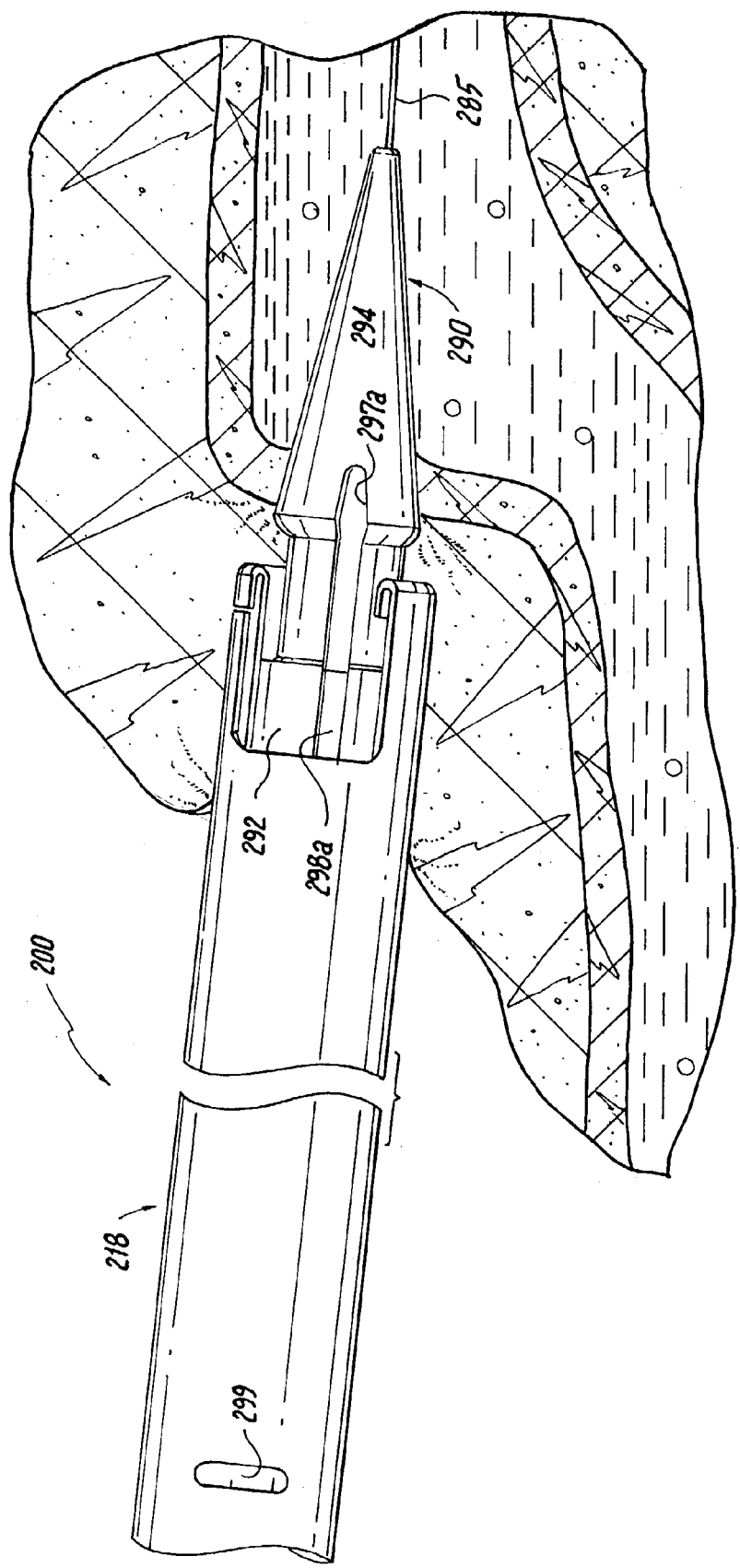
FIG. 43 illustrates the distal end portion of the vascular suturing device of FIG. 42 with the vascular introducer extending partially through the incision in the wall of a blood vessel along a guidewire.

Referring to FIGS. 43 and 44, in use, the vascular dilator 290 of suturing device 200 is guided into through the incision in the wall of a blood vessel along guidewire 285 extending through bore 293. As the distal portion 294 passes through the incision, blood flow through the incision is obstructed, as seen in FIG. 43. However, when the distal end portion 294 extends a sufficient distance through the wall of the blood vessel such that the three inlet slots (e.g., inlet slot 297a) are positioned within the blood vessel, blood will surge through the inlet slots, and into the corresponding and aligned longitudinal grooves 298–298c communicating with annular groove 296. The blood will then flow to the observation port(s) 299, whereupon the surgeon or an assistant will observe that the distal end of the instrument is in an operational position for suturing the blood vessel to close the incision therein.

As shown in FIG. 44, at this time, the wall of the blood vessel envelopes the annular channel 296 in dilator 290 to provide a tactile sensation or indication to the surgeon, and in addition, the wall of the blood vessel is gathered within the opposed U-shaped tissue engagement areas 260a, 260b formed in the distal end portions of the inner and outer tubular members 226 and 222. As a result, the portions of the longitudinal grooves 298a–298c that extend through the annular groove 296 are enveloped by the wall of the blood vessel. Thus, the blood will remain within the longitudinal grooves and will not escape through the tissue engagement areas 260a, 260b.

Referring now to FIGS. 45 and 46, there is illustrated a variant of vascular suturing device 200. In this embodiment of the suturing device, the three longitudinal grooves 298a–298c formed in the body portion 292 of dilator 290 extend to the proximal end of body portion 218 so that the flow of blood may be observed at the rear end of handle portion 212.

Figure 53:
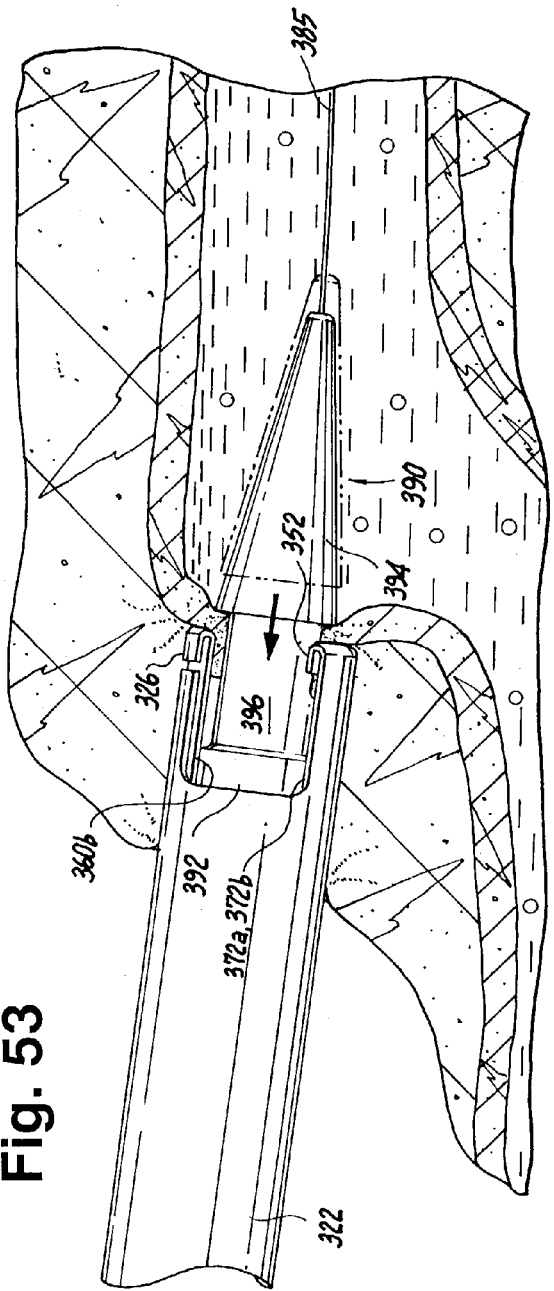
FIG. 53 illustrates the distal end portion of the vascular suturing device of FIG. 47, with the vascular introducer extending through the incision in the wall of a blood vessel and in the retracted position such that the vessel wall is retained between the distal tip portion of the introducer and the inner tubular member and tissue is gathered within the tissue receiving areas formed in the outer tubular member.

Referring to FIGS. 47 through 54, there is illustrated another vascular suturing device constructed in accordance with a preferred embodiment of the subject invention which is designated generally by reference numeral 300. Suturing device 300 is substantially similar to suturing devices 10, 100 and 200 in that it includes an outer tubular member 322, a central tubular member 324 and an inner tubular member 326. As shown in FIGS. 51 and 53, the inner tubular member 326 has an arcuate needle carrying channel 356 formed at a distal end thereof for carrying a pair of arcuate suture needles in back-to-back orientation. The central tubular member 324 has a distal driving stem 354 extending into the channel of the inner tubular member 326 and positioned between the pair of suture needles for sequentially driving the suture needles from the channel of the inner tubular member 326 upon rotation of the central tubular member 324 relative to the inner tubular member 326. The outer tubular member 322 has an arcuate needle reception channel 352 formed at a distal end thereof for receiving the pair of arcuate suture needles after the suture needles have been sequentially driven from the arcuate channel of the inner tubular member 326 by the driving stem of the central tubular member 324. The outer tubular member 322 also has a pair of diametrically opposed tissue receiving recesses 372a and 372b formed in the distal end thereof in which tissue is to be gathered for suturing.

Figure 47:
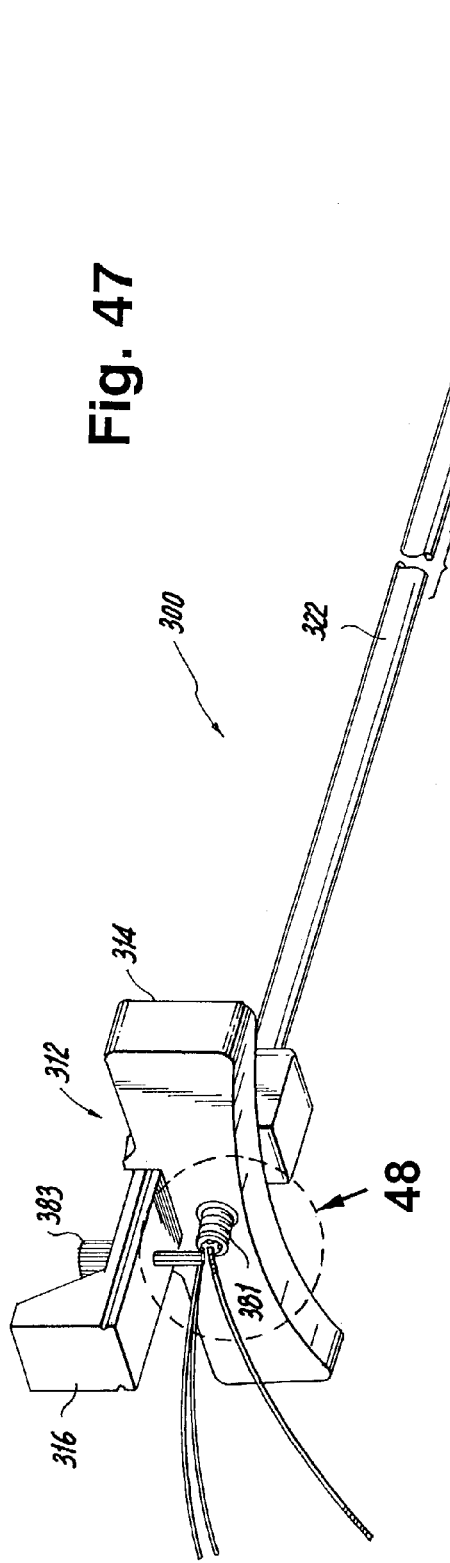
FIG. 47 is a perspective view of a vascular suturing device constructed in accordance with an alternative embodiment of the subject invention.

As shown in FIG. 47, suturing device 300 also includes a handle portion 312 having a stationary handle 314 and an actuator 316 that is operatively associated with a proximal end portion of the outer tubular member 322, the central tubular member 324 and the inner tubular member 326. Actuator 316 effectuates the relative movement of the inner tubular member 326 and the central tubular member 324 relative to the outer tubular member 322 so as to cause sequential passing of the suture needles from the arcuate channel of the inner tubular member 326 to the arcuate channel of the outer tubular member 322. The relative movement of the tubular members is accomplished by cooperative overlying cam slots, and a cam pin that extends through the cooperative overlying cam slots to cause the inner tubular member and the central tubular member to rotate relative to the outer tubular member, as described hereinabove with respect to suturing device 10.

Suturing device 300 differs from suturing device 10 in that it includes an integral vascular dilator 390 that functions to guide the introduction of suturing device 300 through an incision in the wall of a blood vessel. Still further, unlike the previously described suturing devices, suturing device 300 includes a helical spring 381 for biasing the dilator 390 in a retracted position and a retaining pin 383 for securing the dilator 390 in the extended position and for preventing the inner tubular member 326 and central tubular member 324 from rotating relative to the outer tubular member 322.

Vascular dilator 390 is formed from the same or similar material as the other components of the suturing device and includes an elongated body portion 392 disposed within the central lumen of inner tubular member 326. Vascular dilator 390 further includes a tapered distal tip portion 394 that is dimensioned to extend beyond the distal end of the inner tubular member 326 for positioning the distal end of the suturing device 300 at the incision in the wall of a blood vessel.

Figure 48:
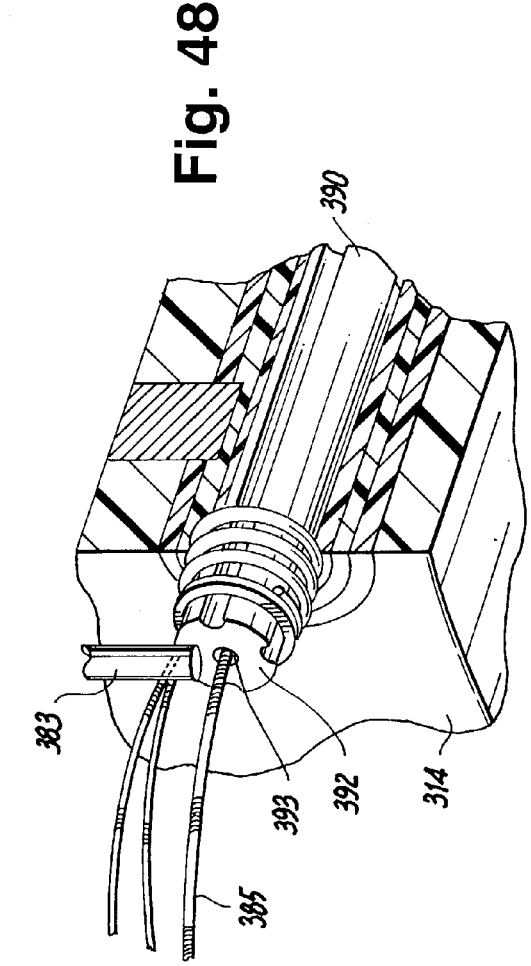
FIG. 48 is an enlarged localized perspective view of the rear end portion of the suturing device of FIG. 47 illustrating the helical spring and retaining pin associated with the proximal end of the vascular introducer.
Figure 49:
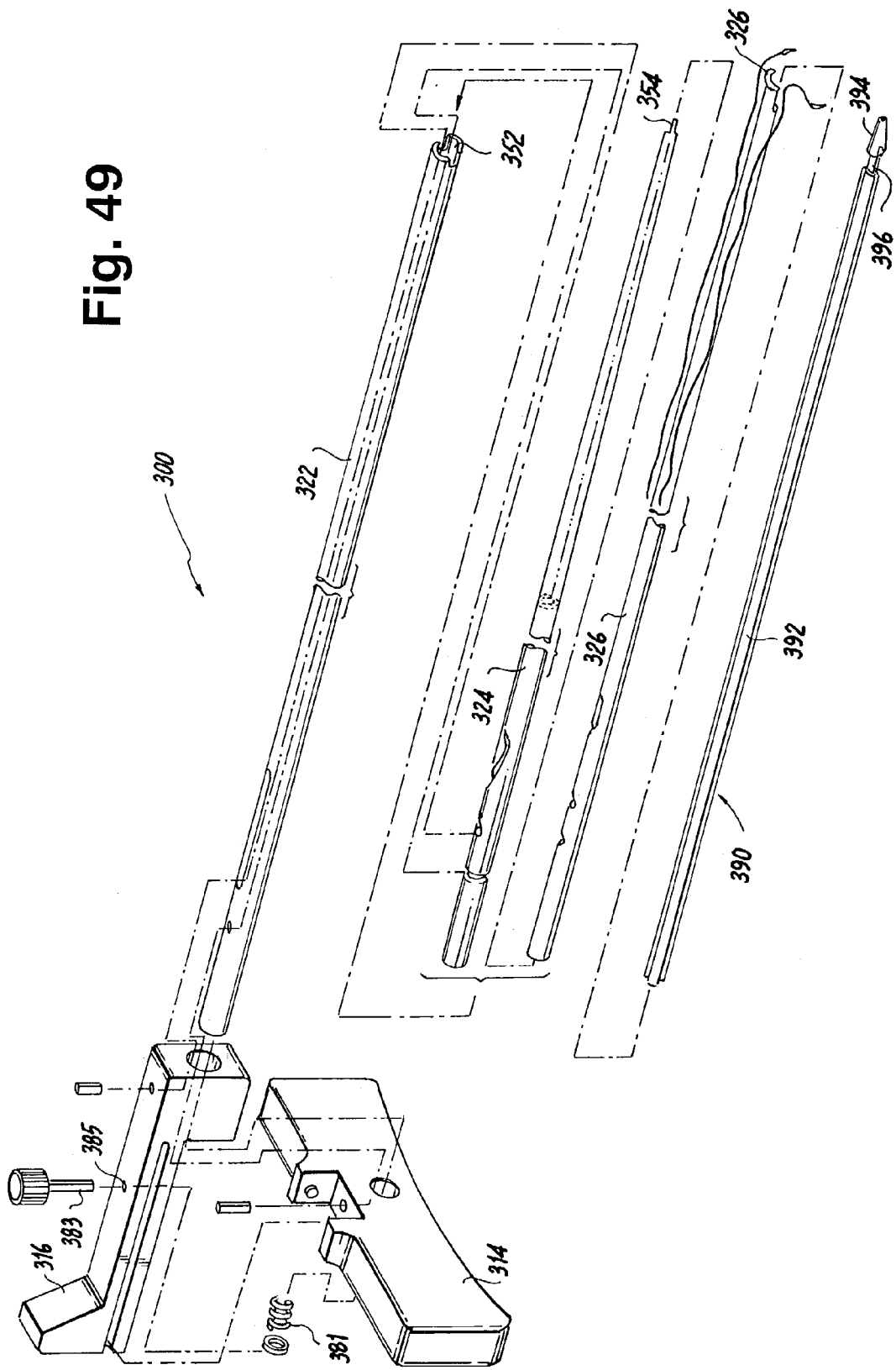
FIG. 49 is an exploded perspective view of the vascular suturing device of FIG. 47 with parts separated for ease of illustration.
Figure 52:
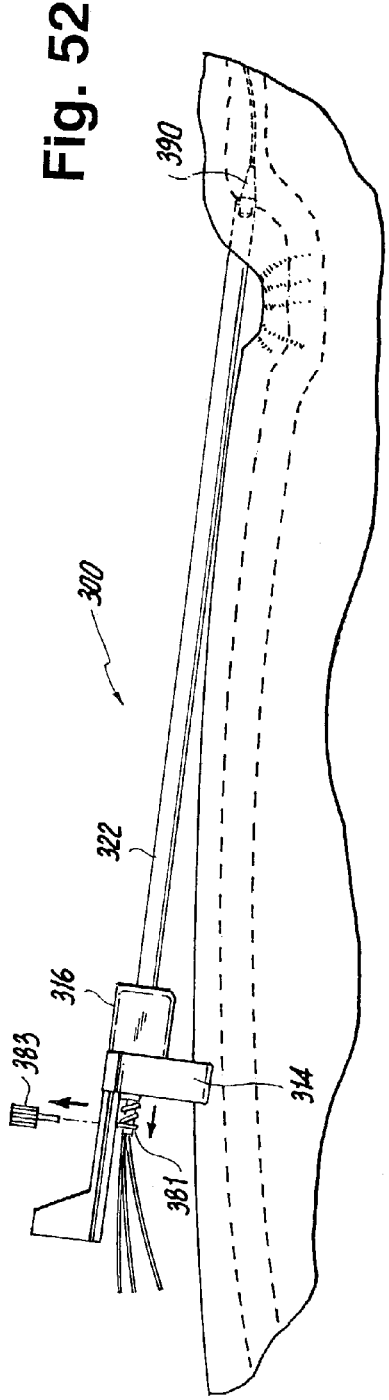
FIG. 52 illustrates the vascular suturing device positioned at the incision site of the blood vessel, wherein the retaining pin which secures the introducer in the extended position has been removed allowing the spring element to urge the dilator in the retracted position.

Vascular dilator 390 is mounted for slidable movement within the central lumen of the inner tubular member 326 of the suturing device 300 between and extended position and a retracted position. An annular groove 396 is formed in the body portion 392 of the dilator adjacent to the tapered distal tip portion 394. As shown in FIGS. 47 and 48, vascular dilator 390 has a central lumen 393 extending therethrough to accommodate a guidewire 385.

When the dilator 390 is in the extended position, annular groove 396 is exposed, i.e., the annular groove 396 is positioned beyond the distal end of the inner tubular member 326. In the retracted position, the distal tip portion 394 of the dilator 390 is positioned as close as practical to the distal end of the inner tubular member 326 and the annular groove 396 is concealed within the central lumen of the inner tubular member 326.

As illustrated in FIG. 51, annular groove 396 is configured and positioned to accept and become enveloped by the wall of the blood vessel. Consequently, the surgeon holding suturing device 300 will be provided with a tactile sensation, indicating that the suturing device 300 has reached its operating position against the wall of the blood vessel.

As stated above, unlike suturing devices 10, 100 and 200, suturing device 300 includes helical spring 381 and retaining pin 383, which are operatively associated with the proximal end of the dilator 390. Helical spring 381 is used to bias the dilator 390 in the retracted position. Retaining pin 383 performs two functions; first, it secures the dilator 390 in the extended position and second, it functions as a lockout mechanism which prevents the axial movement of the actuator 316 thereby preventing the rotation of the inner tubular member 326 and central tubular member 324 relative to the outer tubular member 322. Those skilled in the art would readily appreciate that a separate device could be used for each function.

In operation, the vascular dilator 390 of suturing device 200 is guided into through the incision in the wall of a blood vessel along guidewire 285 extending through bore 293. During the insertion process, retaining pin 383 is engaged within aperture 385 and therefore, the dilator 390 is secured in the extended position and the actuator 316 is prevented from moving relative to the stationary support member 314 (see FIG. 51). When the exposed annular groove 396 reaches the wall of the blood vessel, the surgeon holding suturing device 300 will be provided with a tactile sensation, indicating that the suturing device 300 has reached its operating position against the wall of the blood vessel. At this time, the wall of the blood vessel envelopes (i.e., prolapses into) the annular channel 396 in dilator 390 to provide the tactile sensation. Additionally, the wall of the blood vessel is gathered within the opposed U-shaped tissue receiving recesses 372a and 372b formed in the distal end portion of the outer tubular member 322.

At this point, the surgeon removes retaining pin 383 from within aperture 385 provided in actuator 316. As a result, helical spring 381 urges the dilator 390 into the retracted position. As shown in FIG. 53, when the dilator 390 is biased into the retracted position, the wall of the blood vessel which has been enveloped within annular channel 396 and has been gathered in tissue engagement areas 372a and 372b is further urged into the tissue engagement areas 372a and 372b and is held therein by virtue of being captured between the distal tip portion 394 of dilator 390 and the inner and outer tubular members 326 and 322, respectively. After the retaining pin 383 has been removed and the dilator 390 has secured the tissue, the surgeon operates the suturing device 300 in a manner which is similar to the previously described embodiments.

Figure 54:
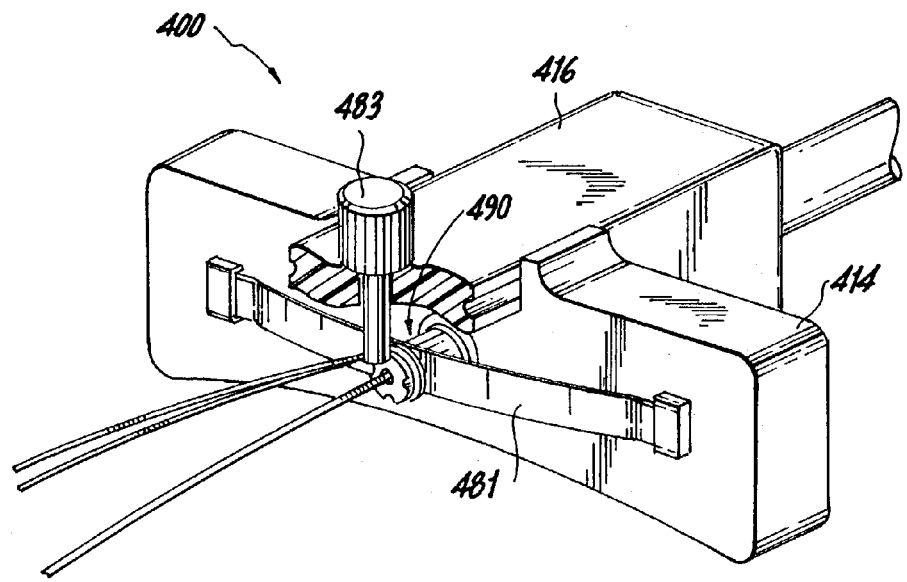
FIG. 54 is an enlarged localized perspective view of the rear end portion of an alternative embodiment of the vascular suturing device of the subject invention illustrating a leaf spring element and retaining pin associated with the proximal end of the vascular introducer.
Figure 55:
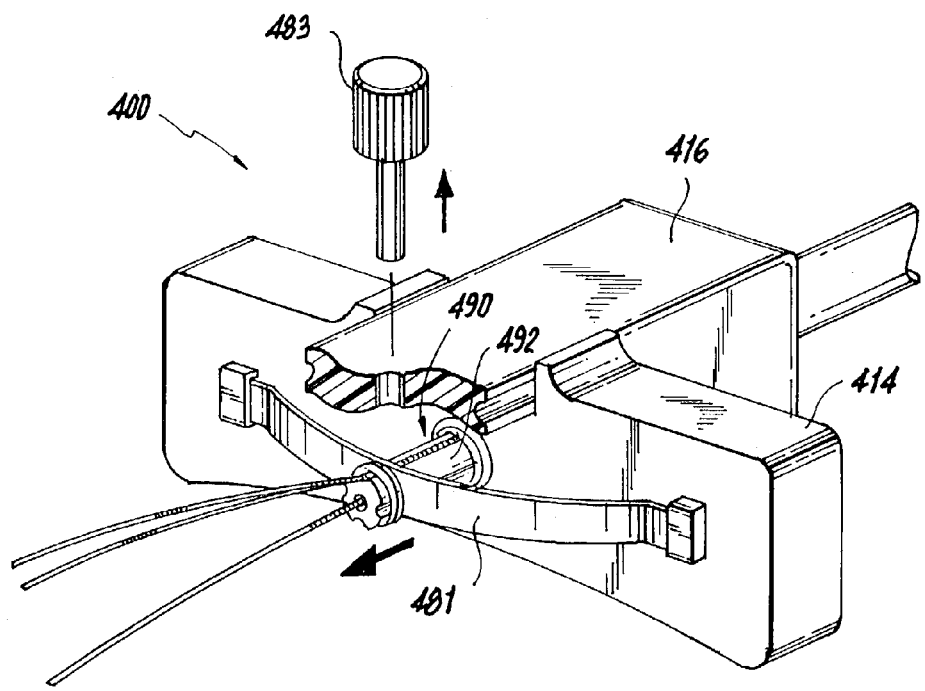
FIG. 55 is an enlarged localized perspective view of the rear end portion of an the vascular suturing device of FIG. 54 wherein the retaining pin has been removed and the leaf spring element is urging the introducer in the retracted position.

Referring now to FIGS. 54 and 55, there is illustrated another vascular suturing device constructed in accordance with a preferred embodiment of the subject invention which is designated generally by reference numeral 400. Suturing device 400 is substantially similar to suturing device 300 in that it includes an integral vascular dilator 490 having an elongated body portion 492 which is slidably disposed within the central bore of an inner tubular member. However, unlike suturing device 300, the mechanism used for biasing dilator 490 in the retracted position includes a leaf spring 481 rather than a helical spring element. Leaf spring 481 is attached to the stationary handle 414 at opposed longitudinal ends thereof. As before, a retaining pin 483 operatively associated with the distal end of dilator 490 and actuator 416 is used to secure the dilator 490 in the extended position and function as a lockout mechanism while the suturing device 400 is being inserted into the incision formed in the blood vessel wall.

Although the vascular suturing apparatus of the subject invention has been described with respect to preferred embodiments, those skilled in the art will readily appreciate that changes and modifications may be made thereto without departing from the spirit and scope of the present invention.

What is claimed is:

1. A suturing device comprising:
a) an inner tubular member having an arcuate needle carrying channel formed at a distal end thereof carrying a pair of arcuate suture needles in back-to-back orientation;
b) a central tubular member having a distal driving stem extending into the needle carrying channel of the inner tubular member and positioned between the pair of suture needles for sequentially driving the suture needles from the needle carrying channel upon rotation of the central tubular member relative to the inner tubular member;
c) an outer tubular member having a pair of diametrically opposed tissue receiving recesses formed in a distal end of the tube wall and an arcuate needle reception disposed between the tissue receiving recesses and configured for receiving the arcuate suture needles after the suture needles have been sequentially driven from the arcuate channel of the inner tubular member by the driving stem of the central tubular member through tissue gathered within the tissue receiving recesses; and
d) a vascular dilator having an elongated body portion and a tapered distal tip portion, the elongated body portion being slidably disposed within the inner tubular member and having an annular groove formed therein adjacent to the distal tip portion, the distal tip portion extending beyond the distal end of the inner tubular member for positioning the suturing device at an incision in the wall of a blood vessel, the dilator mounted for movement between an extended position in which the annular groove is exposed allowing tissue to prolapse therein so as to provide tactile feedback and a retracted position in which the prolapsed tissue within the annular groove is urged in a proximal direction and gathered within the tissue receiving recesses of the outer tubular member.

2. A suturing device as recited in claim 1, further comprising a handle portion operatively associated a proximal end portion of the outer tubular member, the central tubular member and the inner tubular member for co-axially supporting the outer tubular member, the central tubular member and the inner tubular member.

3. A suturing device as recited in claim 2, further comprising means operatively associated with the handle portion and a proximal end of the dilator for biasing the dilator in the retracted position.

4. A suturing device as recited in claim 3, wherein the means for biasing the dilator in the retracted position includes a helical spring element engaged with the proximal end of the dilator.

5. A suturing device as recited in claim 3, wherein the means for biasing the dilator in the retracted position includes a leaf spring element engaged with the proximal end of the dilator.

6. A suturing device as recited in claim 2, further comprising means operatively associated with the handle portion and a proximal end of the dilator for retaining the dilator in the extended position.

7. A suturing device as recited in claim 6, wherein the means for retaining the dilator in the extended position includes a pin which is operatively associated with a proximal end of the dilator so as to restrain its axial movement.

8. A suturing device as recited in claim 2, further comprising means operatively associated with the handle portion and a proximal end of the dilator for preventing rotation of the inner tubular member and central tubular member relative to the outer tubular member.

9. A suturing device as recited in claim 2, wherein the handle portion further comprising an actuator operatively associated with the proximal end portion of the outer tubular member, the central tubular member and the inner tubular member for effectuating the relative movement of the inner tubular member and the central tubular member relative to the outer tubular member so as to cause sequential passing of the suture needles from the arcuate channel of the inner tubular member to the arcuate channel of the outer tubular member.

10. A suturing device as recited in claim 9, wherein the inner tubular member, the central tubular member and the outer tubular member include cooperative overlying cam slots, and a cam pin extends through the cooperative overlying cam slots to cause the inner tubular member and the central tubular member to rotate relative to the outer tubular member.

11. A suturing device as recited in claim 10, wherein the cam pin is operatively connected to the actuator.

12. A suturing device as recited in claim 9, wherein the handle portion includes a stationary support portion and the actuator is mounted for movement relative to a stationary support portion.

13. A suturing device as recited in claim 1, wherein the vascular dilator has a central lumen extending therethrough which is dimensioned and configured to accommodate a guidewire.

14. A suturing device as recited in claim 1, further comprising an elongated suture extending between the pair of arcuate suture needles.

15. A suturing device comprising:
   a) an inner tubular member having an arcuate needle carrying channel formed at a distal end thereof carrying a pair of arcuate suture needles in back-to-back orientation;
   b) a central tubular member having a distal driving stem extending into the needle carrying channel of the inner tubular member and positioned between the pair of suture needles for sequentially driving the suture needles from the needle carrying channel upon rotation of the central tubular member relative to the inner tubular member;
   c) an outer tubular member having a pair of diametrically opposed tissue receiving recesses formed in a distal end of the tube wall and an arcuate needle reception disposed between the tissue receiving recesses and configured for receiving the arcuate suture needles after the suture needles have been sequentially driven from the arcuate channel of the inner tubular member by the driving stem of the central tubular member through tissue gathered within the tissue receiving recesses;
   d) a vascular dilator having an elongated body portion and a tapered distal tip portion, the elongated body portion being slidably disposed within the inner tubular member and having an annular groove formed therein adjacent to the distal tip portion, the distal tip portion extending beyond the distal end of the inner tubular member for positioning the suturing device at an incision in the wall of a blood vessel, the dilator mounted for movement between an extended position in which the annular groove is exposed allowing tissue to prolapse therein so as to provide tactile feedback and a retracted position in which the prolapsed tissue within the annular groove is urged in a proximal direction and gathered within the tissue receiving recesses of the outer tubular member;
   e) a handle portion operatively associated a proximal end portion of the outer tubular member, the central tubular member and the inner tubular member for co-axially supporting the outer tubular member, the central tubular member and the inner tubular member;
   f) means operatively associated with the handle portion and a proximal end of the dilator for biasing the dilator in the retracted position; and
   g) means operatively associated with the handle portion and a proximal end of the dilator for retaining the dilator in the extended position and for preventing rotation of the inner tubular member and central tubular member relative to the outer tubular member.

16. A suturing device as recited in claim 15, wherein the means for biasing the dilator in the retracted position includes a helical spring element engaged with the proximal end of the dilator.

17. A suturing device as recited in claim 15, wherein the means for biasing the dilator in the retracted position includes a leaf spring element engaged with the proximal end of the dilator.

18. A suturing device as recited in claim 15, wherein the means for retaining the dilator in the extended position includes a pin which is operatively associated with a proximal end of the dilator so as to restrain its axial movement.

19. A suturing device as recited in claim 15, wherein the vascular dilator has a central lumen extending therethrough which is dimensioned and configured to accommodate a guidewire.

20. A suturing device as recited in claim 15, wherein the handle portion further comprising an actuator operatively associated with the proximal end portion of the outer tubular member, the central tubular member and the inner tubular member for effectuating the relative movement of the inner tubular member and the central tubular member relative to the outer tubular member so as to cause sequential passing of the suture needles from the arcuate channel of the inner tubular member to the arcuate channel of the outer tubular member.

21. A suturing device as recited in claim 20, wherein the inner tubular member, the central tubular member and the outer tubular member include cooperative overlying cam slots, and a cam pin extends through the cooperative overlying cam slots to cause the inner tubular member and the central tubular member to rotate relative to the outer tubular member.

22. A suturing device as recited in claim 21, wherein the cam pin is operatively connected to the actuator.

23. A suturing device as recited in claim 20, wherein the handle portion includes a stationary support portion and the actuator is mounted for movement relative to a stationary support portion.

24. A suturing device as recited in claim 15, further comprising an elongated suture extending between the pair of arcuate suture needles.

\* \* \* \* \*